(12) United States Patent
Schenk et al.

(10) Patent No.: US 6,391,639 B1
(45) Date of Patent: May 21, 2002

(54) PLANT AND VIRAL PROMOTERS

(75) Inventors: Peer Martin Philipp Schenk, Tennyson (AU); László Sagi, Heverlee (BE); Serge Remy, Neerpelt (BE); Rony Leon Swennen, Blanden (BE); Ralf Georg Dietzgen, Buderim (AU); Andrew David William Geering, Sinnamon Park (AU); Lee Anne McMichael, Indooroopilly (AU); John Edwin Thomas, Corinda (AU); Christopher Peter Leslie Grof, The Gap (AU); Adrian Ross Elliott, Auchenflower (AU)

(73) Assignee: Commonwealth Scientific and Industrial Research Organization, Campbell (AU)

( * ) Notice: Subject to any disclaimer, the term of this patent is extended or adjusted under 35 U.S.C. 154(b) by 0 days.

(21) Appl. No.: 09/446,821

(22) PCT Filed: Jun. 26, 1998

(86) PCT No.: PCT/AU98/00493

§ 371 Date: Apr. 17, 2000

§ 102(e) Date: Apr. 17, 2000

(87) PCT Pub. No.: WO99/00492

PCT Pub. Date: Jan. 7, 1999

(30) Foreign Application Priority Data

Jun. 26, 1997 (AU) ............................................. PO 7593

(51) Int. Cl.$^7$ .......................... C12N 5/04; C12N 15/82; C12Q 1/68; C07H 21/04; A01H 19/34

(52) U.S. Cl. .......................... 435/419; 435/6; 435/69.1; 435/91.1; 435/468; 536/23.1; 536/24.1; 800/298

(58) Field of Search .......................... 435/6, 69.1, 91.1, 435/468, 410, 419, 320.1; 536/23.1, 24.1, 25.3

(56) References Cited

PUBLICATIONS

G. Harper et al., Banana streak virus coding regions, Genbank Accession No. AJ002234 Submitted Nov. 18, 1997.

Lynda S. Hagen et al., Nucleotide Sequence and Genomic Organization of Cacao Swollen Shoot Virus, *Virology*, vol. 196, 1993, pp. 619–628.

*Primary Examiner*—Sean McGarry
*Assistant Examiner*—Jane Zara

(57) ABSTRACT

The invention provides plant and viral promoters that can be used to confer high-level gene expression on transgenic plants. Representative promoters can be isolated from the genome of Australian banana-infecting badnaviruses from cultivars Mysore, Williams and Goldfinger. The invention further provides construct which include the disclosed promoters operatively linked to a coding sequence. Still further provided are a method of expressing the product of a gene in a plant cell, plant cells having DNA constructs within their genomes, and plants comprising the transgenic cells.

16 Claims, 18 Drawing Sheets

```
1651 TTCAATTCTG TAAATGGCAG ACAGAGTGAG GTGTCAAAGG ACGATGGGGC
                                                 ─────────
                                                   GATA-1
1701 CCAATGAGTA CCCGCTTTGA CTACTTTACA ATCTGAAAGC TATGCTTTTA
1751 TTTTGTTAAG CTGATCCTGA GCCTCGGGGA GCCGGATCTA GCATAGTAAA
                ─────────
                  GATA-1
1801 ACCAGAGGCG CCCCTGGTAT TGGCGCTGCG GTTTAAGCC  CACGGTTTTC
1851 GGACTCCATG AGTTTTGAAA TCCGACGGCT TTAGTCTGAG AAGGCTCAGC
                ─────────  ────────
                  C/EBP
1901 CTTTCTCTAT ATAAGGGTTT GTAACCCCTC GTTGCAAGCA GAGTCGGAAA
     ──────────  ────
       0  TATA
1951 TACCAGACTG CTTACTTCGA GTTTTGAAAT CCCAATAAGA ATCCTCAGTT
     ────
      INI
2001 TTCTTTCATCC TTCTTTTCGGT TCACTTCCTG AAAATTGGGCA AGCCCCATAG
2051 TAAGGAAAGA TCCATTTGGT TTCACTCCCTG GTAATTCCGC GTATCAGAGC
2101 CATGT
```

*Fig. 16*

```
851   CCATGACGTA GCGGAAGTGA TGGACCCCAT ACCACTGGAT GGCACTAACC
901   AGTGTGACAA GGATACGAGA TGCCAAGTGA GCTGGATAGC ACTCACTTTA
951   TGTAAAGAGT GGTCTGCGTA CCAACTCCAC TATAGTCTGT CTGAGGTGCG
1001  ATGCTGTGTC ACGCACAAAG ACTTTAGATT CCTTTGCCGTG AGATGTACGC
      GATA-1
1051  AAAGCAGTGT GTCCAGAGTG TGCTGTGACG CGTCCCTTGC ATTATTGGTG
                                       ATF
1101  GGTGCACCTA ACGATGCGGG AAGCCGAACT CCCTCTATAA ATAGGACCCC
                                                 TATA
1151  GTGTATTCAG TTGCAAGCAC GCAACACAAC GCGAGCTTAC TTCTGAGAAG
                                       INI
1201  AAATAAGAAC AATTTGTGCT TGAAATACAC CTTGTGTCAA GAGTGTGAGT
1251  AGAGCGCAAG ATCCGTGTTG GGAAATCCGT GCCGTTCTGG AAATCCGTGC
1301  CGTTCTGGTA TCAGAGCTTT GT
```

*Fig. 17*

```
 901  CTTACTTCAC CGGGTTCATT ATTAAAGAGC CTTTACAGCT CATACCCTTA
 951  TTAATAATGT TAGTGCTTGT ACTATTGTGC TTTGCCAGCA CATACTGGCG
1001  TGTAAAGGCA TCTGGTTGTC CCCAGAAGGC CTAAAGTTAG TGCGTTCCAA
1051  CGCACATCTG TGTGTAAAGG TATCTGGCTG TTTCCAGACG CTACCTCCCT
                        C/EBP
1101  CTTTTCTCCT CCCGTCCATA TAAGGAGGCA GAACCTAAGT GTTTCAGGCA
                                 TATA
1151  TCGAGGGAAA TACCCATCTG CCTAATCCAC TTCCAGTGTT TTCCAAAGCA
                              0
1201  GCTGAAGTTT TCAGTCTGTG AGTAGAAAGC AAGATCCTTG TAAGAATTTT
                      INI
1251  TGAGAAGTTT ATATTTGATT TCTCCCCATC TGGTATCAGA GCGATAT
```

*Fig. 18*

PLANT AND VIRAL PROMOTERS

This application is the U.S. National phase under 35 U.S.C. § 371 of International Application PCT/EP98/00493, filed Jun. 26, 1998, which claims priority of Australia application AU PO 7593, filed Jun. 26, 1997.

TECHNICAL FIELD

This invention relates to plant and viral promoters that confer high level gene expression on transgenic plants harbouring the promoters. The invention also relates to utilisation of the promoters in the construction of recombinant genes for plant transformation to enable expression at a certain time in a certain tissue and at a certain rate. In particular, the invention relates to promoters isolated from different isolates of banana-infecting badnaviruses.

BACKGROUND ART

Genetic engineering of plants has proven to be an alternative method for plant breeding and for the introduction of new desirable traits that are reflected in altered phenotypes. In addition, it provides a valuable tool for biological research. Plant genetic manipulation focuses on the cellular level of organisation and involves the interfacing of all aspects of cell biology, molecular biology and gene transfer procedures (Sharp et al., *Food Technology*, February 1984, pp. 112–119). The genetic engineering tools of tissue culture, somaclonal and gametoclonal variation, cellular selection procedures and recombinant DNA are either indirectly or directly concerned with the enhanced expression and transfer of genes. An essential problem for this is the choice of a suitable promoter that results in the desired rate, location and time of gene expression. In the majority of applications of plant genetic engineering, a strong promoter is required to ensure that a sufficient amount of gene product is expressed. These applications include genetic manipulation of plants to obtain disease resistance or tolerance against plant-infecting viruses, bacteria, fungi or nematodes, to obtain resistance against herbivores, to obtain resistance against herbicides, heavy metals and selectable marker reagents, to obtain resistance against abiotic factors (e.g., draught, salt, cold, and anaerobic conditions) to conduct functional analyses of genes and gene products for research, to confer silencing or enhancement of genes and gene products (modulation of gene expression), to modify the composition of macromolecules and secondary metabolites (e.g., to increase nutritional value or to alter structural composition), to modify plant development, and to improve fruit or crop quality. (e.g., post harvest shelf life or disease resistance).

The function and mode of action of promoters have been studied extensively in both monocot and dicot plants. In most cases reporter genes such as the uidA gene encoding for β-glucuronidase (GUS: Jefferson et al., *EMBO J.* 6, 3901–3907 [1987]) or genes encoding anthocyanin production or the jellyfish green fluorescent protein (GFP; Chalfie et al., *Science* 263, 802–805 [1994]) are used to assay promoter activity in transient or stable gene expression systems. Promoters derived from monocot species often do not exhibit a regulated pattern of expression in transgenic dicots, whereas in transgenic monocots, they show a highly regulated expression (Shimamoto, *Current Opinion in Biotechnology*, 5, 158–162 [1994]). Highly regulated expression patterns have been demonstrated for several promoters in transgenic monocots, even though there is no absolute specificity. These include light-inducible and leaf-specific promoters, seed-specific promoters, meristem-specific promoters, root-specific promoters, flower-specific promoters, hormone-inducible promoters, pathogen-inducible promoters and constitutive promoters. Within monocot and dicot plants it has been shove that promoters derived from species of the same group reveal the same or similar highly regulated expression pattern (Shimamoto, 1994, supra).

For many purposes in plant genetic engineering, a strong nearly constitutive promoter is required to ensure sufficient expression throughout the plant. Several strong nearly constitutive promoters for the genetic manipulation of plants have been patented (e.g., the 35S promoter of cauliflower mosaic virus—see U.S. Pat. No. 5,352,605, U.S. Pat. No. 5,164,316, U.S. Pat. No. 5,196,525. U.S. Pat. No. 5,322,938 and U.S. Pat. No. 5,359,142). However, having more than one nearly constitutive promoter can be very useful when several different genes need to be expressed in plants (gene pyramiding). It has been frequently observed that gene silencing occurs in plants transformed with several genes that are each regulated by the same promoter (Flavell, *Proc. Natl. Acad. Sci. USA* 91, 3490–3496 [1994]; Finnegan and McElroy, *Bio/Technology* 12, 883–888 [1994]; Matzke et al., *Mol. Gen. Genet.* 244, 219–229 [1994]: Park et al., *The Plant Journal* 9, 183–194 [1996]). This problem is thought to be caused by homology-based genetic interference and can be avoided using different promoters for gene pyramiding.

SUMMARY OF THE INVENTION

It is an object of the present invention to provide promoters operative in plant cells which can be used in genetic engineering for regulation of gene expression.

It is a further object of the invention to provide at least part of a chimaeric gene comprising one or more of the described promoters operatively linked to DNA encoding an RNA and/or polypeptide.

According to a first embodiment of the invention, there is provided a promoter operative in a plant cell, said promoter comprising:

1) isolated DNA from a badnavirus having a sequence as defined by SEQ ID NO: 1, SEQ ID NO: 2 or SEQ ID NO: 3;
2) isolated DNA which is a viral homologue or a plant genome-derived variant of the DNA of (1).
3) a promoter-active portion of the isolated DNA of (1) or (2);
4) an isolated DNA which hybridises under stringent conditions to the DNA of (1) or (2); or
5) a promoter-active portion of the isolated DNA of (4).

According to a second embodiment of the invention, there is provided a DNA construct comprising at least one gene having at least one promoter according to the first embodiment operatively linked to a coding sequence.

According to a third embodiment of the invention, there is provided a DNA construct comprising:

1) a first gene having at least one promoter according to the first embodiment operatively linked to a coding sequence; and
2) a second gene having a promoter operatively linked to a coding sequence, wherein the expression product of said second gene coding sequence modulates activity of the expression product of said first gene coding sequence.

According to a fourth embodiment of the invention, there is provided a method of expressing a product in a plant cell, said method comprising introducing a DNA construct according to the second embodiment or an RNA transcript of said construct into cells of a plant, wherein said DNA construct or RNA transcript coding sequence encodes said product.

According to a fifth embodiment of the invention, there is provided a plant cell, wherein the genome of said plant cell includes a DNA construct according to the second embodiment or the third embodiment.

According to a sixth embodiment of the invention, there is provided a plant, plant tissue or reproductive material of a plant, wherein said plant, plant tissue or reproductive material comprises cells according to the fifth embodiment.

BRIEF DESCRIPTION OF THE DRAWINGS

FIGS. 16 to 18 depict putative promoter elements in the promoters pMy, pCv and pGo derived from the sequences presented as SEQ ID NO: 1, SEQ ID NO: 2 and SEQ ID NO: 3, respectively.

BEST MODE AND OTHER MODES OF PERFORMING THE INVENTION

Figure 1:
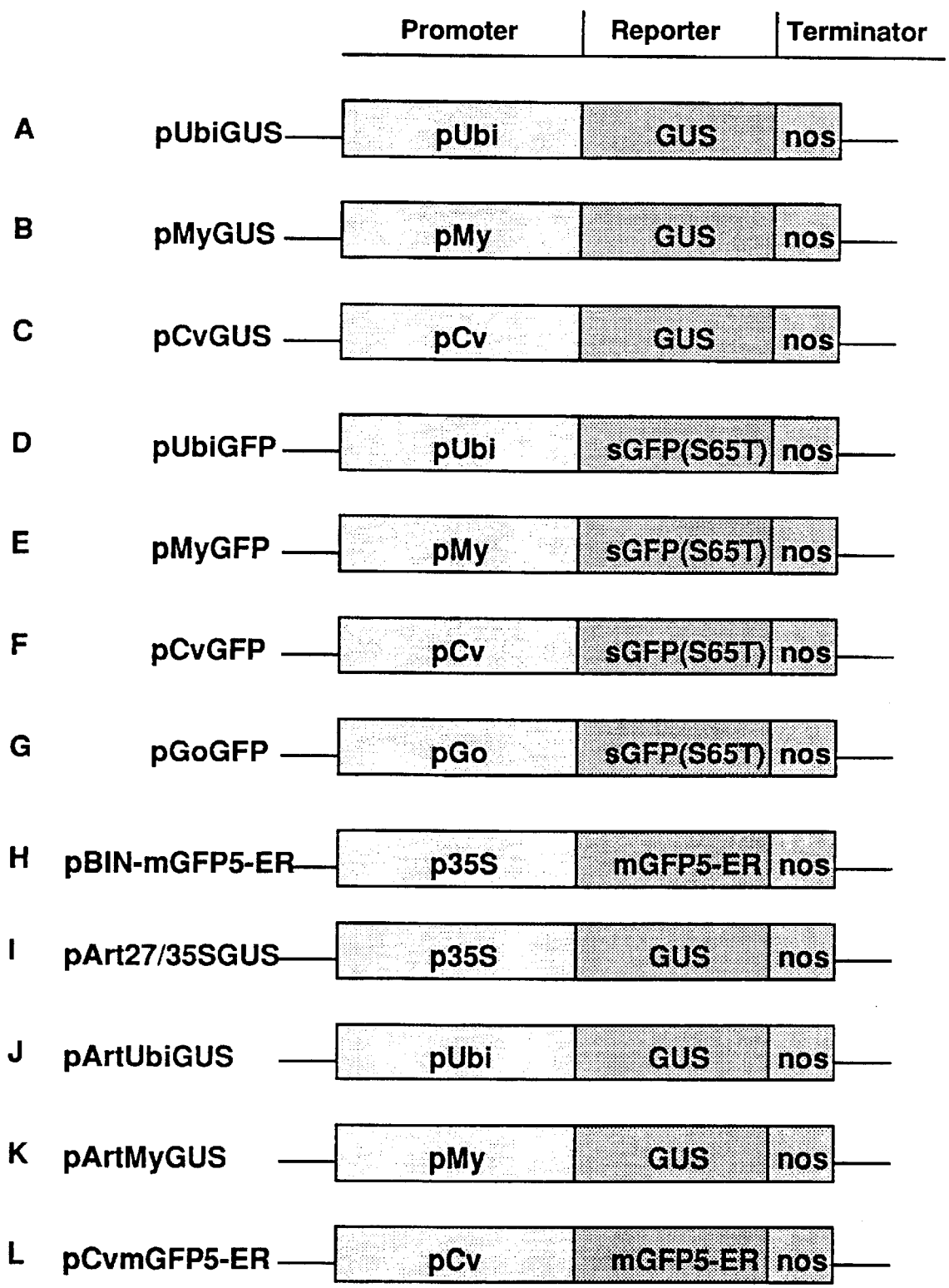
FIG. 1 presents promoter-reporter gene constructs comprising promoter regions from the Australian banana-infecting badnavirus isolates from cultivars Mysore (My), Cavendish-type Williams (Cv) and Goldfinger (Go) in fusion with reporter genes (GUS or GFP).

The following abbreviations are used through this specification:

| | |
|---|---|
| ER | endoplasmatic reticulum |
| GFP | green fluorescent protein of jellyfish *Aequorea victoria* |
| GUS | β-glucuronidase of Escherichia coli |
| MU | 4-methylumbelliferone |
| MUG | 4-methylumbelliferyl-β-D-glucuronide |
| Nos | nopaline synthase terminator of Agrobacterium tumefaciens |
| p35S | cauliflower mosaic virus 35S promoter |
| PCR | polymerase chain reaction |
| pCv | promoter region according to the sequence of SEQ ID NO: 2 |
| PEG | polyethylene glycol |
| pGO | promoter region according to the sequence of SEQ ID NO: 3 |
| pMy | promoter region according to the sequence of SEQ ID NO: 1 |
| pUbi | maize ubiquitin promoter. |
| ScBV | sugarcane bacilliform badnavirus |

So that terms used throughout the description will have a clear and consistent meaning, the following definitions are provided:

Badnavirus: Bacilliform DNA virus.

Coding sequence: A nucleic acid sequence that encodes a functional RNA transcript, which may or may not be subsequently translated into a polypeptide.

Constitutive promoter: A promoter, which is active in the majority of cells in an organism. By use of the term nearly constitutive it is implied that the promoter will be in most cases active in all types of cells during plant development, but may be active at a different rate in different types of cells during different stages of plant development.

Homologue: A nucleic acid sequence from another organism or virus isolate that has a sequence identity (homology) of 60% or more with the sequence of SEQ ID NO: 1 over nucleotides 1538–2105, SEQ ID NO: 2 over nucleotides 850–1322 or SEQ ID NO: 3 over nucleotides 859–1297, or parts thereof that are longer than 200 bp, and has substantially the same function as the DNA sequence corresponding to SEQ ID NO: 1, SEQ ID NO: 2 or SEQ ID NO: 3. Preferably, the homologue has a sequence identity of at least 70%, or more preferably, 75%.

Plant genome-derived variant: DNA that is present in a plant genome and has a sequence identity (homology) of 60% or more with the sequence of SEQ ID NO: 1 (nucleotides 1538–2105), SEQ ID NO: 2 (nucleotides 850–1322) or SEQ ID NO: 3 (nucleotides 859–1297), or parts thereof that are longer than 200 bp. Preferably, the plant genome-derived variant has a sequence identity of at least 70%, or more preferably, 75%.

Promoter: A DNA sequence flanking the coding sequence of a gene at the 5' end thereof which includes an element or elements involved in the initiation of transcription of the coding sequence.

The one letter code for nucleotides in DNA conforms to the IUPAC-IUB standard described in *The Biochemical Journal* 219:345–373 (1984). Percentages in the examples are given in weight/volume (w/v) unless otherwise stated.

The present inventors have identified three promoter sequences in PCR-amplified cDNA sequences of the viral genome of Australian banana-infecting badnaviruses from cultivars Mysore, Williams and Goldfinger.

These promoters, as well as homologues from banana-infecting badnaviruses and plant genome-derived variants, can be used separately or in combination in conjunction with appropriate coding sequences to prepare transgenic plants capable of expression of the gene(s) of interest at a suitable level.

DNA comprising the three promoters according to the invention can be obtained by cloning viral DNA from the genome of badnaviruses, such as the Australian banana-infecting badnavirus isolates from cultivars Mysore, Williams and Goldfinger. Badnavirus DNA isolated from infected Australian banana plants (cultivars Mysore, Williams and Goldfinger) can be fragmented with restriction enzymes and fragments can be subcloned into plasmids that can be multiplied in a host cell such as *Escherichia coli*. Alternatively, these promoter sequences can be generated by direct polymerase chain reaction (PCR) amplification of genomic DNA. The required primers can be designed from the sequence data of SEQ ID NO: 1, SEQ ID NO: 2 and SEQ ID NO: 3. Yet another method of producing promoters having sequences such as those present in SEQ ID NO: 1, SEQ ID NO: 2 and SEQ ID NO: 3 is by DNA synthesis. This is particularly the case if a promoter-active portion of a larger promoter sequence is desired where oligonucleotides of 10 to 100 nucleotides can be conveniently synthesised. Complementary oligonucleotides can also be synthetised to form a double-stranded molecule of the desired nucleotide sequence.

As indicated above, the invention comprises not only promoters having the sequence of SEQ ID NO: 1, SEQ ID NO: 2 or SEQ ID NO: 3 but also homologues from banana-infecting badnaviruses and plant genome-derived variants (e.g. of plant genome-integrated badnaviruses or retrotransposons) of the SEQ ID NO: 1, SEQ ID NO: 2 or SEQ ID NO: 3 sequences. The invention further includes DNAs which hybridises with DNA comprising nucleotides 1538–2105, nucleotides 850–1322 or nucleotides 859–1297 of SEQ ID NO: 1, SEQ ID NO: 2 or SEQ ID NO: 3, respectively, under stringent conditions. Homologues and plant genome-derived variants can have identity with the DNA sequences of SEQ ID NO: 1 (nucleotides 1538–2105) or SEQ ID NO: 2 (nucleotides 850–1322) or SEQ ID NO: 3 (nucleotides 859–1297) as low as about 60%. The stringent conditions under which a promoter according to the invention will hybridise with the DNA sequence of SEQ ID NO: 1 (nucleotides 1538–2105) or SEQ ID NO: 2 (nucleotides 850–1322) or SEQ ID NO: 3 (nucleotides 859–1297) can be defined as follows:

Wash solution —0.1×SSPE, 0.1% SDS

Wash temperature —65° C.

Number of washes—two (1×SSPE is 180 mM NaCl, 10 mM $NaH_2PO_4$, 1 mM EDTA (pH 7.4))

Preferred promoter-active portions of promoter sequences of the invention are nucleotides 1538–2105 of SEQ ID NO: 1, nucleotides 850–1322 of SEQ ID NO: 2, and nucleotides 859–1297 of SEQ ID NO: 3. Even more preferred are nucleotides 1806–2105 SEQ ID NO: 1, nucleotides 1023–1322 of SEQ ID NO: 2, and nucleotides 998–1297 of SEQ ID NO: 3.

DNA constructs according to the second and third embodiments can include more than one promoter operatively-linked to the coding sequence. These additional promoters can be identical promoters, derivatives of the same promoter, or heterologous promoters. In addition, operatively linked regulatory elements such as enhancers or silencers can be included in DNA constructs.

In the DNA constructs of the second and third embodiments, the coding sequence to which the promoter or promoters are operatively linked can encode an RNA which functions as antisense RNA, a ribozyme or as a structural component, or is translated into a polypeptide which functions as an enzyme, a structural component or has some other physiological effect. The coding sequence can encode more than one RNA or more than one polypeptide. Furthermore, the coding region can encode a combination of at least one RNA and at least one polypeptide. Examples of transgene products which can be usefully expressed in transgenic plants using promoters according to the invention are products that help:

1) to obtain disease resistance or tolerance against plant-infecting viruses, bacteria, fungi or nematodes.

2) to obtain resistance against herbivores, 3) to obtain resistance against herbicides, heavy metals or selectable marker reagents.

4) to confer resistance against abiotic factors (e.g. draught, salt, cold, anaerobic conditions), 5) to conduct functional analyses of genes and gene products for research, 6) to confer silencing or enhancement of genes and gene products (modulation of gene expression), 7) to modify the composition of macromolecules and secondary metabolites (e.g. to increase nutritional value or to alter structural composition), 8) to modify plant development, or 9) to improve fruit or crop quality (e.g. post harvest shelf life or disease resistance).

With reference to the third embodiment of the invention, the first gene of the DNA construct includes all the variations and options of the gene comprising the DNA construct of the second embodiment. The second gene of the DNA construct can have an expression product which either:

1) complements or enhances the effect of the expression product of the first gene;

2) counteracts the expression product of the first gene; or 3) modifies the activity of the first gene promoter(s).

These options allow a high regulation of gene expression by linkage of a second gene with the strong expression mediated by the promoter(s) of the first gene.

It will be noted from the Summary of the Invention that the invention includes transgenic plant cells with genetically engineered genomes including the DNA constructs of the second and third embodiments. These DNA constructs can also comprise recombinant viral sequences with one or more coding sequences of interest that either stably or transiently express in plant cells. Alternatively, RNA transcripts can be made from these constructs that can be used for transformation of plant cells.

Techniques for introducing DNA into the genome of a plant are well known in the art and are described, for example by Sági et al., (*Bio/Technology* 13, 481–485 [1995]), May et al. (*Bio/Technology* 13, 485–492 [1995]), Zhong et al., *Plant Physiol*. 110, 1097–1107 [1996]).

DNA constructs according to the invention are advantageously introduced into the genome of target plant cells using methods including Agrobacterium-mediated transformation, biolistic bombardment with DNA-coated tungsten or gold particles, electroporated or polyethyleneglycol (PEG)-mediated DNA transformation of protoplasts, vacuum infiltration and other mechanical DNA transfer techniques. Transgenic plant cells including the DNA constructs of the invention can be propagated using conditions appropriate to the particular plant. Similarly, whole plants, or propagating material of the plant, can be prepared from the initial transgenic cells using known methods and conditions.

Promoters according to the invention can be used in monocotelydonous and dicotelydonous plants as well as in gymnosperms and ferns. For example, the promoters are active in the following monocot species: sugarcane, banana, maize, millet, sorghum. Dicot species in which promoters of the invention are active include tobacco, canola, Tipu tree and *Nicotiana benthamiana*. Gymnosperm and fern species in which promoters according to the invention are active include radiata pine and fishbone fern, respectively.

So that the invention may be better understood, several non-limiting examples follow.

General Methods

Manipulation of DNA was carried out using known methods such as those described by Sambrook et al. (*Molecular Cloning: a Laboratory Manual*, 2nd Ed., Cold Spring Harbour Laboratory Press, Cold Spring Harbour N.Y. [1989], the entire content of which is incorporated herein by cross-reference). Reagents and other material were obtained from commercial sources or as otherwise indicated.

EXAMPLE 1

Cloning of the Novel Promoters

Badnavirus isolates were obtained from infected leaf material from banana cultivars Mysore (Musa group AAB)

and Williams (Musa group AAA) from the Centre for Wet Tropics Agriculture, South Johnstone, North Queensland, Australia and Goldfinger (Musa group AAAB) from a field at Deeral, North Queensland, Australia.

Badnavirus virions from cultivar Mysore were isolated using a modified protocol used for the purification of cocoa swollen shoot badnavirus (Lot et al., *J. Gen. Virol.* 72, 1735–1739 [1991]). Laminar tissue was homogenised by blending in 6 volumes of extraction buffer (50 mM $NaH_2PO_4/Na_2HPO_4$ buffer (pH 6.1) containing 5 mM sodium diethyldithiocarbamate (DIECA), 0.2% thioglycerol, 0.5% polyethylene glycol (PEG) 6000 and 0.5% (v/v) celluclast (Novo Industries). An additional 2 volumes of extraction buffer was added and the preparation shaken at 100 rpm at room temperature for 5 h and incubated overnight at 4° C. The homogenate was filtered through four layers of cheesecloth and the filtrate centifuged at 3,950 rpm (3,000×g) for 20 min at 10° C. in an SW HS4 rotor (Sorvall). NaCl to 0.2 M and PEG 6000 to 9.5% were added to the supernatant which was stirred for 15 min and then kept for 3 h at room temperature. The PEG precipitate was pelleted by centrifugation at 7,000 rpm (10,000×g) for 20 min at 10° C. in an SW HS4 rotor. The pellet was resuspended in 1/30 original extration volume of resuspension buffer (50 mM $NaH_2PO_4/Na_2HPO_4$, pH 6.8, containing 0.2 M NaCl, 0.1% $Na_2SO_3$ and 5 mM EDTA). The suspension was clarified by centrifugation at 8,180 rpm (8,000×g) in an SS34 rotor (Sorvall), the supernatant retained and the pellet again resuspended in 1/30 original extraction volume of resuspension buffer. The centrifugation was repeated the supernatants pooled and the final pellet discarded. Celite (2 g per 30 g of starting material) was added to the supernatant, mixed and filtered under gentle suction through a Buchner funnel. NaCl to 0.2 M and PEG 6000 to 7% was added to the filtrate and the mixture transferred to a 4 cm celite column. The column was prepared in a 2 cm diameter 30 ml syringe, and was equilibrated with resuspension buffer. The virus was eluted under gentle suction with the stepwise addition of 25 ml aliquots of resuspension buffer containing 5%, 3%, 1% then 0% PEG 6000. The eluate from each step was centrifuged at 6,950 rpm (7,000×g) for 10 min at 10° C. in an SA 600 rotor (Sorvall), and the supernatant centrifuged at 50,000 rpm (25,500×g) for 50 min in a 70 Ti rotor (Beckman). Pellets were resuspended in 100 $\mu$l 50 mM tri-sodium citrate buffer pH 7.0, an aliquot stained with equal volume of 2% potassium phosphotungstate negative stain and examined by electron microscopy for the presence of virus.

Virus-containing fractions were pooled and layered onto 10–40% sucrose density gradients in citrate buffer and centrifuged at 35,000 rpm (16,500×g) in an SW 41 rotor (Beckman). The gradients were fractionated using an ISCO fractionator monitoring absorbance at 254 nm, and taking 0.5 ml fractions. Fractions under peaks of absorbance were pooled, diluted in citrate buffer and pelleted by centrifugation at 53,000 rpm (29,000×g) for 30 min at 4° C. in a 75 Ti rotor (Beckman). Pellets were resuspended in 50 $\mu$l citrate buffer, an aliquot stained with an equal volume of 2% potassium phosphotungstate solution and examined by electron microscopy for virus concentration and purity.

Virus DNA was prepared using a total nucleic acid extraction method (Lot et al., *J. Gen. Virol.* 72, 1735–1739 [1991]). A proportion of this was fragmented using XhoII and subcloned into pBluescript II SK+(Stratagene) previously cut with BamHI and dephosphorilised. Sequences obtained from these clones were used as the basis for the design of the primer L2838-forward which was used in combination with the degenerate badnaT primer (see reference in Lockhart and Olszewski in *Breeding Bananas and Plantain for Resistance to Diseases and Pests*, pp. 105–113. J. Ganry, ed., Montpellier, France, CIRAD/INIBAP, 1993) for PCR amplification. The sequences of the primers follow.

L2838-forward (SEQ ID NO: 4):
5'-CCC AGG AAT AAA CAC GAT TAT CAG TC-3'
badnaT (SEQ ID NO: 5):
5'-CAC CCC CGG G(A/C)(C/T) (A/C)(A/T)(A/C/G/T) GCT CTG ATA CCA-3'

The PCR mixture (containing 2.5 $\mu$l 10×PCR buffer (Gibco BRL), 0.625 $\mu$l 50 mM $MgCl_2$ solution, 1.125 $\mu$l 20 $\mu$M L2838-forward primer, 2.5 $\mu$l 4 $\mu$M badnaT primer, 0.5 $\mu$l 10 mM dNTPs, 0.2 $\mu$l Taq DNA polymerase (Gibco BRL), 16.55 $\mu$l $H_2O$ and 1 $\mu$l of a 1:200 dilution of purified badnavirus DNA) was incubated in a Hybaid OmniGene Thermocycler (Stratagene) with programming conditions (94° C. 2 min; 35 cycles of 94° C. 0.5 min. 62° C. 0.5 min. 72°C. 2 min) according to the manufacturer's instructions. After electrophoretic separation from other PCR products, a 2 kb product was subcloned into pCR-Script SK+ (Stratagene) according to the manufacturers instructions. This clone was named pCRBSV2.

Badnavirus particles from Cavendish-type cultivar Williams and Goldfinger were prepared using a modified small scale virus particle concentration method of Ahlawat et al., *Plant Disease* 80, 590–592 (1996). Laminar tissue was ground to a powder with a mortar and pestle in liquid nitrogen. Two volumes of miniprep extraction buffer (0.2 M $KH_2PO_4$/ $K_2HPO_4$, pH 7.0, containing 15 mM EDTA, 2% PVP, 2% PEG 6000 and 0.4% $Na_2SO_3$) was added. After an additional grinding, the extract was filtered through four layers of cheesecloth. The filtrate was then centrifuged at 7,000 rpm (10,000×g) for 15 min at 4° C. in an SW HS4 rotor (Sorvall) and the supernatant collected. To the supernatant, a 1/15 volume of 33% (v/v) Triton X-100 was added, the supernatant briefly shaken, then centrifuged through a 5 ml pad of 30% sucrose in 0.2 M $KH_2PO_4$/ $K_2HPO_4$ buffer (pH 7.0) at 45,000 rpm (24,000×g) for 45 min at 4° C. in a 70 Ti rotor (Beckman). The pellet was gently washed with distilled water and resuspended in 100 $\mu$l of 0.1 M $KH_2PO_4/K_2HPO_4$ buffer (pH 7.0). A 30 ml of chloroform was added to the resuspension, emulsified by mixing and the emulsion centrifuged at 13,000 rpm for 5 min in a benchtop microfuge. The supernatant was removed and an aliquot stained with an equal volume of 2% potassium phosphotungstate solution and examined by electron microscopy.

Immunocapture-PCR was carried out in thin-walled 0.6 ml PCR tubes (Quantum) coated with 25 $\mu$l of sugarcane bacilliform virus (ScBV) antibodies (Agdia) in 50 mM sodium carbonate buffer (pH 9.6) at a concentartion of 1 $\mu$g/ml. After incubation for 3 h (4 h for Goldfinger isolate) at room temperature, the tubes were washed by vortexing three times (two times for Goldfinger isolate) with PBST (137 mM NaCl, 6.4 mM $Na_2HPO_4$×2 $H_2O$, 1.4 mM $KH_2PO_4$, pH 7.4, containing 0.1% Tween 20 (Sigma)). After the addition of 25 $\mu$l of concentrated virus extract, tubes were incubated for 3 h at room temperature (overnight at 4° C. for Goldfinger isolate), then washed three times with PBST and one time with $H_2O$ which was removed prior to PCR. The degenerate primers badnaT and badna3 (Lockhart and Olszewski, supra) were used for PCR amplification. The sequence of badna3 follows.

badna3 (SEQ ID NO: 6):
5'-AAT AGC GGC CGC AT(A/C/T) AT(A/C/T) AT(A/C/T) GA(A/G) AC(A/C/G/T) GA-3'

The PCR mixture (containing 5 $\mu$l buffer A (Gibco BRL), 5 $\mu$l buffer B (Gibco BRL), 5 $\mu$l 4 $\mu$M badna3 primer, 5 $\mu$l 4 µM badnaT primer, 2.5 µl 1 mM dNTPs, 2 µl Elongase (Gibco BRL) and 25.5 µl H₂O for the Williams isolate, and 2.5 µl 10×PCR buffer (Gibco BRL), 0.75 µl 50 mM MgCl₂, 2.5 µl 4 µM badna3 primer, 2.5 µl 4 µM badnaT primer, 1.25 µl 1 mM dNTPs, 0.4 µl Taq polymerase (Gibco BRL, 5 units/µl) and 15.1 µl H₂O for the Goldfinger isolate) was added to the tube containing the immuno-captured virus particles, overlaid with 20 µl mineral oil and incubated in an Hybaid OmniGene Thermocycler (Stratagene) with the programming conditions (4 cycles of 94° C. 0.5 min, 37° C. 0.5 min, 72° C. 2 min and 30 cycles of 94° C. 0.5 min, 55° C. 0.5 min, 72° C. 2 min) according to the manufacturers instructions. After electrophoretic separation from other PCR products, 1.3 kb products were subcloned into pCR2.1 (Invitrogen) according to the manufacturers instructions. These clones were named pCRBSVCv (Williams isolate) and pCRGF2 (Goldfinger isolate).

Sequencing was first carried out using primers and primer sites present in the vectors and later in the obtained sequence using the FS Terminator Premix (PRISM Ready Reaction DyeDeoxy Terminator Cycle Sequencing Kit, Applied Biosystems) and an Automated DNA Sequencer (Applied Biosystems). Full length sequences of all three PCR products were obtained and identified as badnavirus sequence using the Australian National Genomic Information Service (ANGIS) program package. The complete sequences of the PCR products are depicted in SEQ ID NO: 1, SEQ ID NO: 2 and SEQ ID NO: 3. All three sequences comprise a coding region for part of the badnavirus ORF 3 at the 3' end (nucleotides 1–1537, 1–849 and 1–858, respectively) and a non-coding region at the 5' end (nucleotides 1538–2105, 850–1322 and 859–1297, respectively). The 3' ends of the non-coding regions were further analysed for promoter sequence elements as will be detailed below in EXAMPLE 5.

EXAMPLE 2

Construction of Chimaeric Genes

Several constructs were made using the above described PCR products as promoters in fusion with reporter genes coding for either GUS or GFP as depicted in FIG. 1.

pUbiGUS was used as the basis for the construction of promoter-reporter cassettes for plant cell transformation using biolistic or PEG-mediated transformation techniques (FIG. 1A). pUbiGUS contains the maize ubiquitin promoter (Christensen et al., *Plant Mol. Biol.* 18, 675–689 [1992]; Christensen and Quail, *Transgen. Res.* 5, 213–218 [1996]), the GUS reporter gene (Jefferson et al., *EMBO J.* 6, 3901–3907 [1987]) and the nopaline synthase (nos) terminator sequence from *Agrobacterium tumefaciens* in pUC118.

pMyGUS contains the badnavirus PCR fragment from Mysore (BadnaT primer at the 3' end) instead of the maize ubiquitin promoter (FIG. 1B). It was constructed by ligating the blunt-ended BamHI/NotI-cut 2 kb fragment from pCRBSV2 into the blunt-ended dephosphorylated BamHI/HindIII-cut 4.8 kb fragment of pUbiGUS.

pCvGUS contains the badnavirus PCR product from Williams (BadnaT primer at the 3' end) instead of the maize ubiquitin promoter (FIG. 1C). It was constructed by ligating the blunt-ended BamHI/NotI-cut 1.3 kb fragment from pCRBSVCv into the blunt-ended dephosphorylated BamHI/HindIII-cut 4.8 kb fragment of pUbiGUS.

In addition, pUbiGFP was used as the basis for the construction of promoter-reporter cassettes for plant cell transformation using biolistic or PEG-mediated transformation techniques (FIG. 1D). pUbiGFP contains the maize ubiquitin promoter, a modified GFP reporter gene (sGFP (S65T); Chiu et al., *Current Biol.* 6, 325–30 [1996]) and a nopaline synthase (nos) terminator sequence.

pMyGFP contains the badnavirus PCR fragment from Mysore (BadnaT primer at the 3' end) instead of the maize ubiquitin promoter (FIG. 1E). It was constructed by ligating the blunt-ended BamHI-cut 2 kb fragment from pCRBSV2 into the blunt-ended dephosphorylated XbaI-cut 4.2 kb fragment of pUbiGFP.

pCvGFP contains the badnavirus PCR product from Williams (BadnaT primer at the 3' end) instead of the maize ubiquitin promoter (FIG. 1F). It was constructed by ligating the XbaI/BamHI-cut 1.3 kb fragment from pCRBSVCv into the dephosphorylated XbaI/BamHI-cut 4.8 kb fragment of pUbiGFP.

pGoGFP contains the badnavirus PCR product from Goldfinger (BadnaT primer at the 3' end) instead of the maize ubiquitin promoter (FIG. 1G). It was constructed by, ligating the EcoRV/BamHI-cut 1.3 kb fragment from pCRGF2 into the EcoRV/BamHI-cut 4.8 kb fragment of pCvGFP.

Furthermore, pBIN-mGFP5-ER and pArt27/35SGUS were used as the basis for the construction of promoter-reporter cassettes for Agrobacterium-mediated plant transformation (FIG. 1H and FIG. 1I, respectively). pBIN-mgfp5-ER (a gift of Dr J. Haseloff, MRC Laboratory of Molecular Biology, Addenbrookes Hospital, Cambridge, UK) contains the cauliflower mosaic virus 35S promoter, the ER-targeted mutated version of the GFP reporter gene mgfp5-ER and the nos terminator, pArt27/35SGUS contains the cauliflower mosaic virus 35S promoter (Odell et al., *Nature* 313, 810–812 [1985]), the GUS reporter gene and the nos terminator in pArt27 (Gleave, *Plant Mol. Biol.* 20, 1203–1207 [1992]). pArtUbiGUS contains the maize ubiquitin promoter instead of the 35S promoter of pArt27/35SGUS (FIG. 1J).

pArtMyGUS contains the badnavirus PCR fragment from Mysore (BadnaT primer at the 3' end) instead of the 35S promoter or the maize ubiquitin promoter (FIG. 1K). It was constructed by ligating the HindIII/BamHI-cut 1.6 kb fragment from pMyGFP into the HindIII- and partially BamHI-cut 13 kb fragment of pArtUbiGUS.

pCvmGFP5-ER contains the badnavirus PCR fragment from Williams (BadnaT primer at the 3' end) instead of the 35S promoter (FIG. 1L). It was constructed by ligating the EcoRV/BamHI-cut 1.3 kb fragment from pCvGFP into the HindIII(blunt-ended)/BamHI-cut 13 kb fragment of pBIN-mgfp5-ER.

All plasmid DNA was prepared from *Escherichia coli* DH5a using the Qiaprep Spin Miniprep Kit (Qiagen).

The chimaeric gene constructs were found to be useful for assessing promoter activity using in vivo transient and stable expression systems that were developed and optimised for this purpose.

EXAMPLE 3

Assaying Promoter Activity in Plant Cells Under Transient Conditions

Several in vivo test systems were available for assaying the promoter-reporter gene constructs of EXAMPLE 2 under transient conditions. These systems were:

1) biolistic gene transfer on leaves and other plant organs of monocot species (banana, maize, millet, sorghum), dicot species (tobacco, canola, *Nicotiana benthamiana, Tipuana tipu*), gymnosperm species (*Pinus radiata*) and fern (*Nephrolepis cordifolia*) using GUS assays;

2) biolistic gene transfer on maize leaves and sugarcane calli using GFP assays; and 3) biolistic gene transfer on maize leaves using comparative GUS assays with an internal standard.

The following method was used for the first test system listed above.

Maize (sweet corn, cv. Iochief Improved), banana (cv. Williams), millet, sorghum and *N. benthamiana* leaves were cut from glasshouse-grown plants and subdivided into pieces of 3–4 cm length. These were surface-sterilised in chlorine solution (0.1% NaOCl, 0.1% Tween 20) for 30 min with gentle agitation. Subsequently they were rinsed with sterile deionised water and placed abaxial-side up on Petrie dishes containing sterile "high-salt MS" medium (MS-medium according to Murashige and Skoog, *Physiologia Plantarum* 15, 473–497 [1962], containing 0.2 M mannitol and 0.2 M sorbitol) for 5 hrs to reduce the cell turgor.

For particle bombardments, leaf pieces were transferred adaxial-side up onto MS-medium as described above without mannitol and sorbitol. Gold particles with a diameter of 1.6 $\mu$m were used as the carrier for DNA. These were prepared by washing in 70% ethanol, vortexing for 3 min, incubating for 15 min and removing the liquid after 30 s of centrifugation. The following step was repeated three times: particles were resuspended in deionised sterile water, vortexed for 1 min. incubated for 1 min and pelleted by centrifugation for 30 s in a microfuge. Subsequently, the gold particles were resuspended in sterile 50% (v/v) glycerol at a concentration of 60 mg/ml and vortexed for 5 min prior to use.

For each plasmid construct used (pMyGUS, pCvGUS and pUbiGUS, EXAMPLE 2), a set of four DNA deliveries was prepared: 50 $\mu$l of the gold particle suspension were transferred into a sterile 1.5 ml centrifuge tube and vortexed thoroughly for another 2.5 min. With the tube continuously vortexed, 10 $\mu$l DNA (0.5 $\mu$g/$\mu$l ), 50 $\mu$l sterile 2.5 M CaCl$_2$ solution and 20 $\mu$l 0.1 M spermidine solution (sterile and stored in 20 $\mu$l aliquots at $-70°$ C. prior to use) were added in that order. The mixture was vortexed for another 2 min, incubated for 1 min and pelleted by centrifugation for 10 s. The pellet was washed in 140 $\mu$l 70% ethanol and 140 $\mu$l 100% ethanol without disturbing the pellet and gently resuspended in 50 $\mu$l 100% ethanol before evenly aliquoting 10 $\mu$l portions onto sterile macrocarrier plastic disks that were subsequently dried in a desiccator. Macrocarriers were placed at a distance of 4 cm from the rupture disc and the prepared leaves were placed 8 cm from the macrocarriers in a PDS-1000/He Biolistic Particle Delivery System (BioRad) which was used for the DNA delivery using pressures between 900 psi and 1,550 psi according to the procedure described by Sandford et al., *Meth. Enzymol.* 217: 483–509 (1993) and Heiser, *BioRad US/EG Bulletin* 1688 (1993).

Leaves and other plant organs of tobacco (cv. Xanthi), canola, tipu tree (*Tipuana tipu*), pine tree (*Pinus radiata*) and fishbone fern (*Nephrolepis cordifolia*) were freshly cut from plants that were grown in glasshouses, growing cabinets and ornamental gardens at the University of Queensland, St. Lucia, Australia. All plant material was placed adaxial side-up in Petrie dishes containing a prewetted round filter paper.

Preparation of gold particles, coating DNA onto gold particles and particle bombardments were carried out according to a modified procedure of Finer et al. (*Plant Cell Rep.* 11:323–328 [1992]) using a custom-made Helium pressure-driven particle inflow gun: 60 mg gold particles were resuspended in 1 mL 70% ethanol for 2 min and subsequently washed by spinning for 10 s in a microfuge and resuspending in deionised water. A stock (to be stored for 6–8 weeks at room temperature) was prepared by centrifugation for 10 s and resuspending of the gold particles in 500 $\mu$l 50% (v/v) glycerol solution. For each construct to be used for particle bombardment, gold particles were vigorously resuspended and 50 $\mu$L were removed to a fresh tube and vortexed for an additional 1 min. During vortexing freshly prepared plasmid DNA (Qiaprep Mini spin kit) was added as a mixture containing 5 $\mu$L (0.25 $\mu$g/$\mu$L) GUS-construct, 50 $\mu$L 2.5 M CaCl$_2$ solution and 20 $\mu$L 0.1 M spermidine solution. After vortexing for an additional minute, particles were allowed to settle for 5–10 min and then centrifuged for 5 s. Excess supernatant was removed and particles were resuspended in 20 $\mu$L of the supernatant. During vortexing, 3 $\mu$L was removed for each bombardment and placed in the centre of a 3 mm Swinney plastic syringe filter holder (Gelman Sciences). Plant material was bombarded at a distance of 18 cm using a Helium-driven pressure of 7 bar (100 psi) and $-0.85$ bar ($-85$ kPa) negative pressure in the chamber.

After bombardment all plant material was kept in a growing cabinet (25° C., 16 hrs of illumination) for 48 hrs before transferring to X-Gluc-solution (1.25 g/l 5-bromo-4-chloro-3-indolyl-$\beta$-D glucuronic acid dissolved in 50 ml/l DMSO), 5 mM ferri cyanide, 5 mM ferro cyanide, 0.3% (v/v) Triton X-100, 10% (v/v) methanol, 10 mM EDTA (pH 8.0), 0.1 M sodium phoshate buffer pH 7.0) for incubation at 37° C. for 12 hrs.

GUS activity measured by the number and size of blue spots was used as indicators for promoter activity. Blue GUS spots appear as black spots in the black and white copies of the photographs provided in the figures. Several sets of experiments were carried out each using the promoter-reporter constructs pMyGUS and pCvGUS. For comparisons, pUbiGUS was included for monocot and pBI221 (a commonly used plant transformation vector containing the CaMV 35S promoter, the GUS reporter gene and the nos promoter, Stratagene) was included for dicot, gymnosperm and fern plant material.

Figure 2:
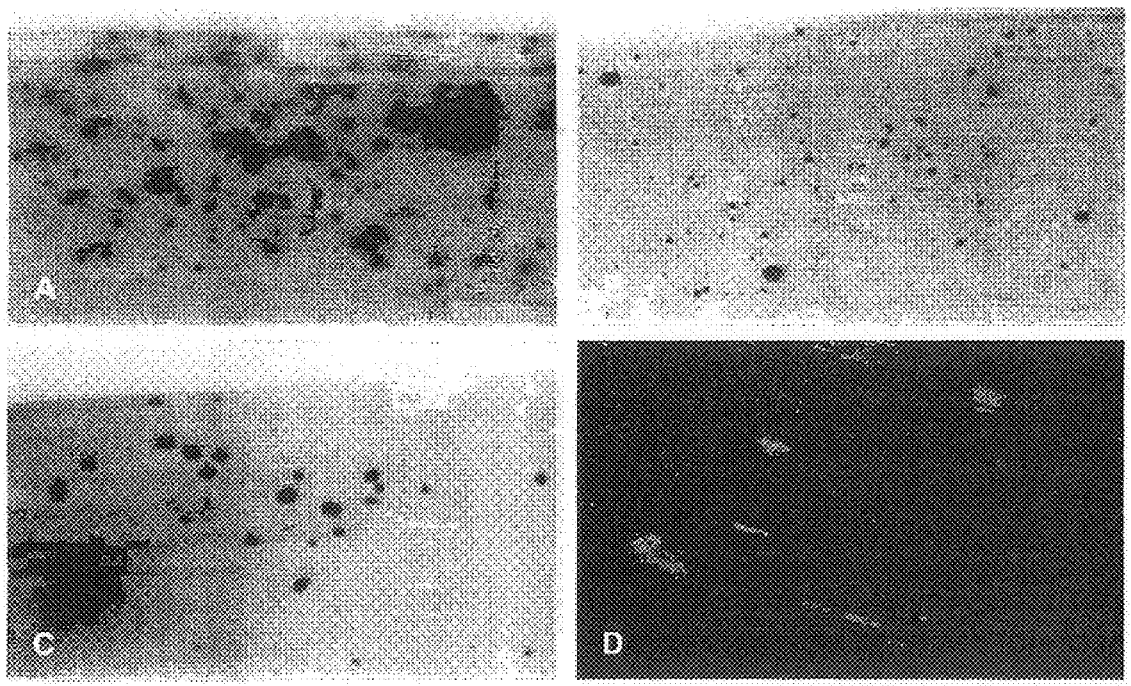
FIGS. 2 to 5 depict the results of transient promoter activity assays using promoter-reporter gene constructs of FIG. 1.
Figure 3:
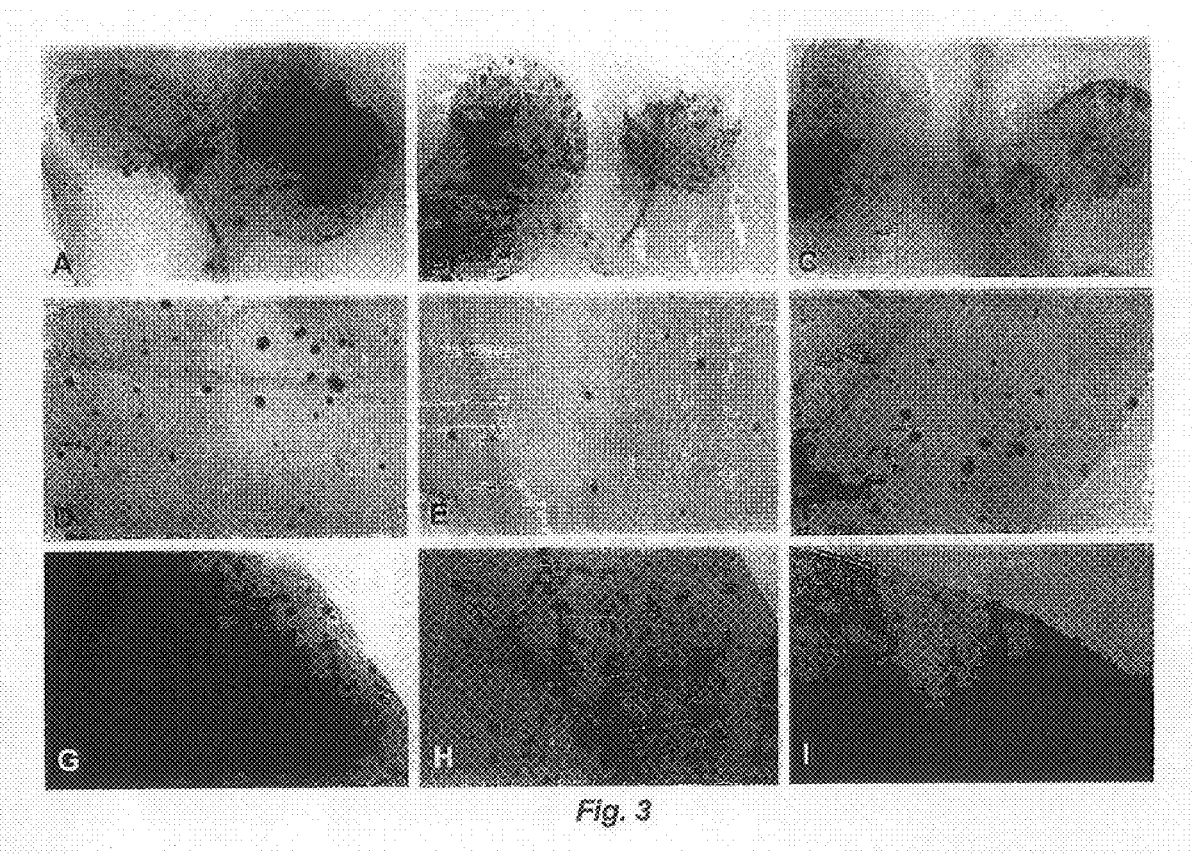
Figure 4:
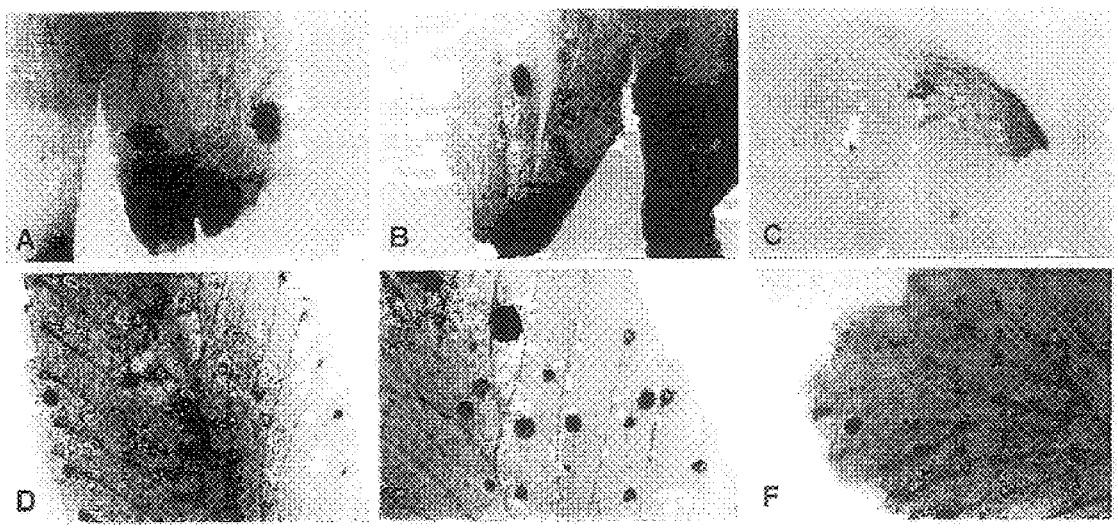

All three promoters (pMy, pCv, and pUbi) used for monocot transient transformation experiments and GUS assays showed clear promoter activities in leaves of maize, banana, millet and sorghum, while control experiments using promoter-free GUS constructs or no DNA showed no activity. As examples, FIG. 2 depicts typical results for maize leaves bombarded with pMyGUS (FIG. 2A), pCvGUS (FIG. 2B) and pUbiGUS (FIG. 2C) at a pressure of 1550 psi. Similarly, all three promoters (pMy, pCv and p35S) used for transient transformation experiments of dicot, gymnosperm and fern species showed clear promoter activities for the plant organs tested. These were leaves of tobacco, *N. benthamiana*, tipu tree and fishbone fern, leaves and stems of canola, and stems and flower petals of male inflorescences of *Pinus radiata*. As examples, FIG. 3 depicts typical results for dicot leaves of canola, tobacco and tipu tree bombarded with pMyGUS (FIG. 3A. FIG. 3D and FIG. 3G, respectively), pCvGUS (FIG. 3B, FIG. 3E and FIG. 3H, respectively) and pBI221 (FIG. 3C, FIG. 3F and FIG. 3I, respectively). FIG. 4 depicts typical results for petals of male inflorescences of *Pinus radiata* and leaves of fishbone fern bombarded with pMyGUS (FIG. 4A and FIG. 4D, respectively), pCvGUS (FIG. 4B and FIG. 4E, respectively) and pBI221 (FIG. 4C and FIG. 4F, respectively). The number and intensity of blue spots generated by transformation with the constructs, pMyGUS and pCvGUS demonstrated that SEQ ID NO: 1 and SEQ ID NO: 2 showed clear promoter activities in all species tested.

The following method was used for the second test system listed above.

Maize leaves were used for particle bombardment with pGoGFP using the particle inflow gun as described above. Visualisation of GFP expression at 24 h after bombardment was achieved using a Leica MZ6 stereo microscope with fluorescence module (Leica Microscopy and Scientific Instruments, Switzerland) with a GFP Plus filter set. The detection of green fluorescing cells was used as an indicator for promoter activity. Green fluorescing cells appear white in the black and white copies of the photographs. The result, depicted in FIG. 2D, demonstrates that SEQ ID NO: 3 had a promoter activity under transient conditions in maize leaves.

Embryogenic sugarcane callus was initiated from young leaf tissue taken from within a 10 cm region just above the apical meristem (Taylor et al., Plant Cell Tissue Organ Cult. 28, 69–78 [1992]). Callus inducing medium (MSC3) consisted of MS salts and vitamins (Sigma), 0.5 g/l casein hydrolysate (Gibco Peptone 140), 20 g/l sucrose, 10% v/v coconut water, 3 mg/l 2,4-D, pH 6.0 and was solidified with 0.8% agar (Grade J. Davis). Calli were induced at 30° C., under continual darkness with regular subculturing every 14 d and required 6 weeks of selective subculturing.

Microprojectile bombardment was performed using a particle inflow gun (Finer et a., Plant Cell Rep. 11, 323–328 [1992]) with 2,100 kPa gas delivery pressure, 28 mmHg vacuum and a 0.5 msec gas delivery interval. Plasmid DNA was precipitated onto tungsten particles (M10, Sylvania Chemicals) and bombardment of individual calli of 5–10 mm diameter in a central area of 7 cm⁻ was performed on osmoticum medium as previously described (Bower et al., Mol. Breeding 2, 239–249 [1996]).

A 5 $\mu$g amount of pMyGFP, pCvGFP or pUbiGFP (EXAMPLE 2) were each used in a mixture with 5 $\mu$g of pEmuKN (Chamberlain et al., Aust. J. Plant Physiol. 21, 95–112 [1994]) for microprojectile bombardment to evaluate promoter activity in sugarcane calli and to allow regeneration of transgenic calli under kanamycin selection (see EXAMPLE 4). GFP expression in sugarcane tissue was visualised at 2 and 7 days and at 2 and 12 months (results of stable expression in EXAMPLE 4) after bombardment using fluorescent microscopy as described above.

Figure 5:
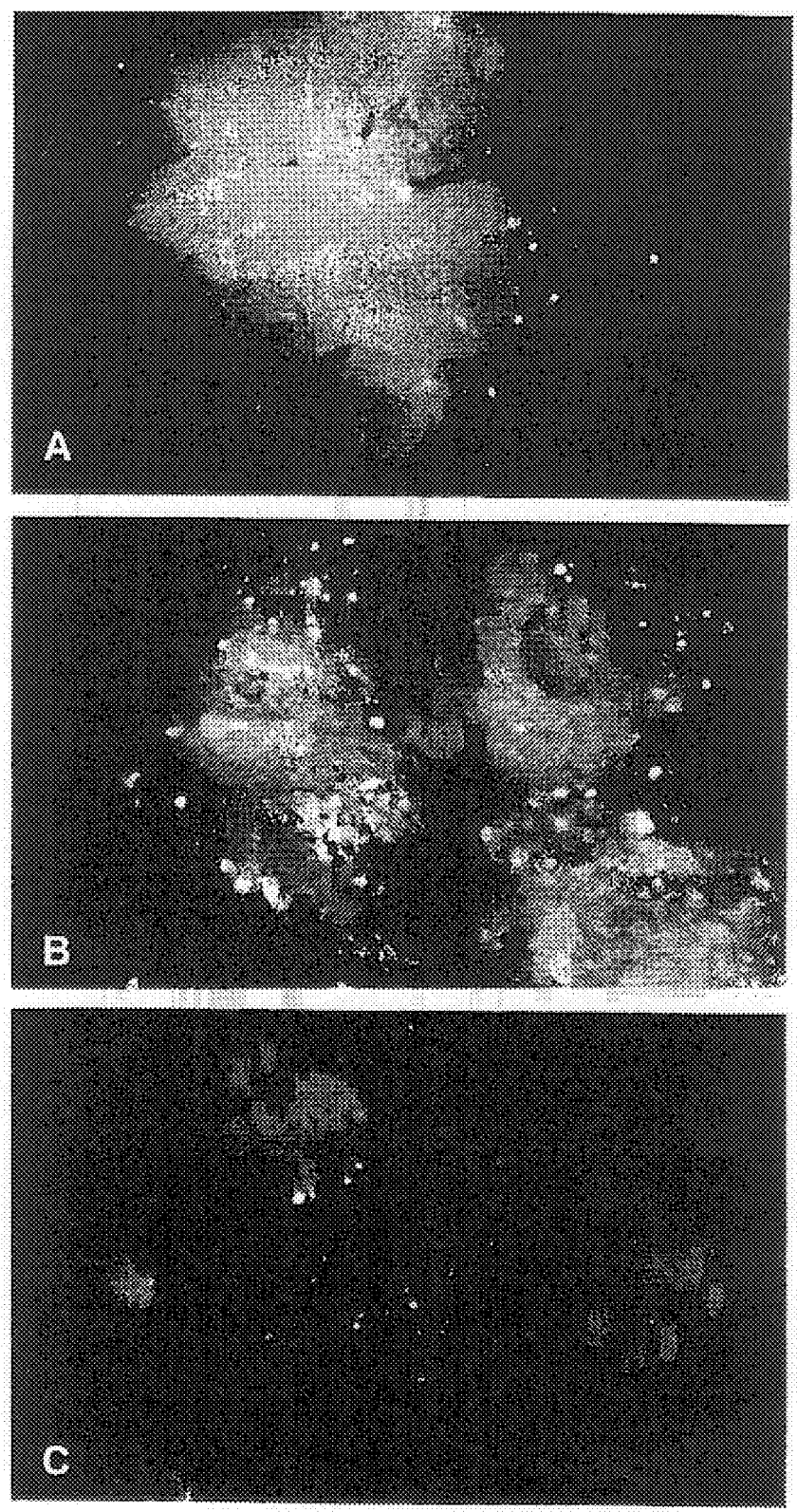

FIG. 5 depicts photographs taken of sugarcane calli bombarded with pMyGFP (FIG. 5A), pCvGFP (FIG. 5B) and pUbiGFP (FIG. 5C) at 2 days after bombardment under fluorescent microscopy. The number and intensity of fluorescing spots of all three constructs pMyGFP, pCvGFP and pUbiGFP, demonstrated that both novel promoters (pMy and pCv) show transient promoter activities in sugarcane calli.

The following method was used for the third test system listed above.

A comparison of pMy and pCv under transient transformation conditions with four other known promoters was performed on maize leaves using the construct pUbiGFP as an internal standard during particle bombardment. The use of an internal standard serves to monitor the effectiveness of each bombardment and compensates for a high variability that is often observed during transient gene expression assays.

Figure 6:
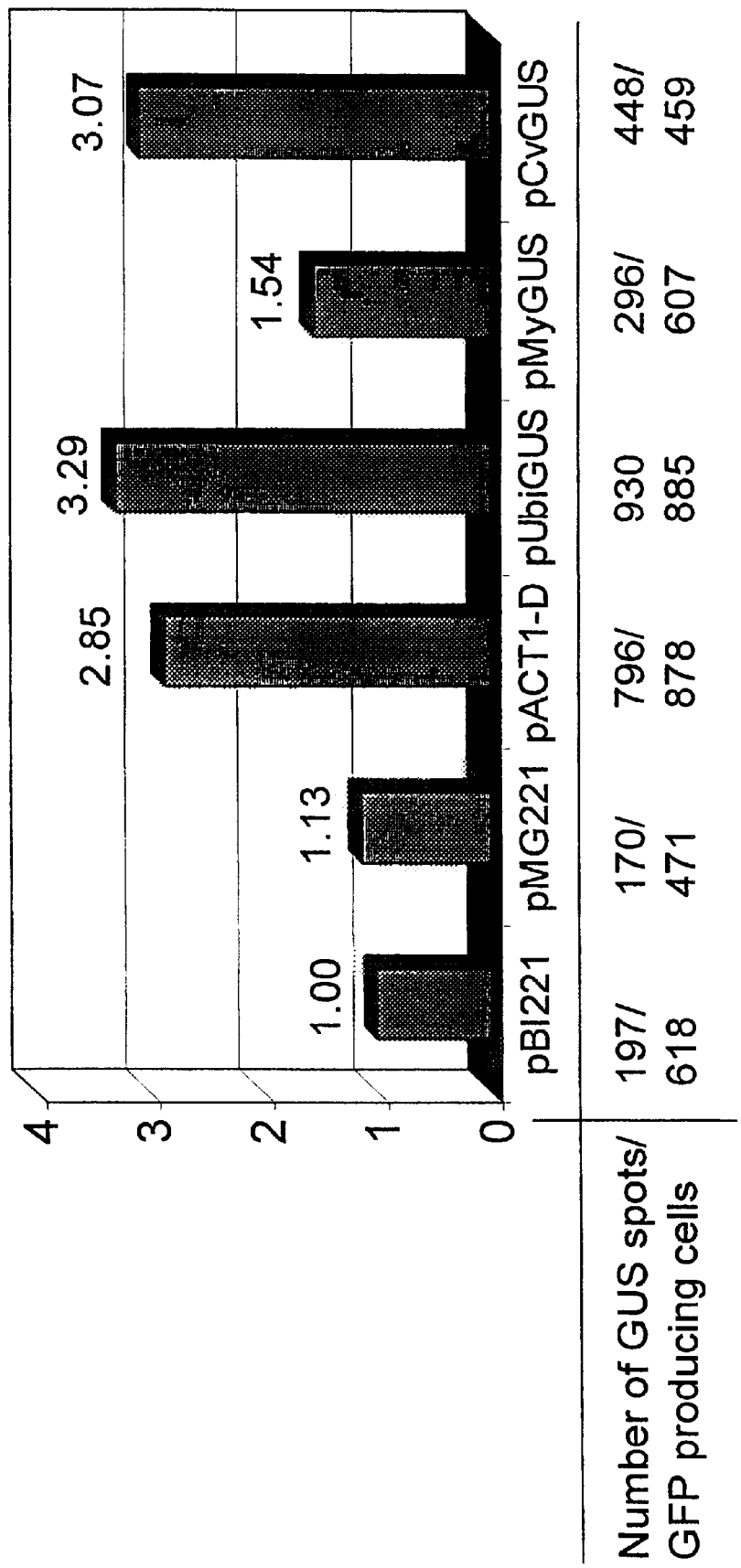
FIG. 6 is a comparison of different promoter activities under standardised transient conditions.

Maize leaves (sweet corn, cv. Iochief Improved) were prepared and used for particle bombardment as described above. The four promoter-GUS constructs used for comparison were pBI221, pMG221, pUbiGUS and pACT1-D that contained the 35S promoter from cauliflower mosaic virus (Mitsuhara et al., Plant Cell Physiol. 37:49–59 [1996]), the enhanced 35S promoter with a 3' exon/intron insertion from the maize shrunken-1 gene (Maas et al., Plant Mol. Biol. 16:199–207 [1991]), the maize polyubiquitin promoter (Christensen and Quail, 1996, supra) and the rice actin 1 gene promoter (McElroy et al., Plant Cell 2:163–171 [1990]), respectively, fused to the uidA gene and a nos terminator. For each experiment a set of four DNA deliveries was prepared for each of the constructs pBI221, pMG221, pUbiGUS, pACT1-D, pMyGUS and pCvGUS as described above with the modification that 0.5 $\mu$L (0.25 $\mu$g/$\mu$L) pUbiGFP was included as internal standard. After 48 h the number of cells producing GFP was determined for all leaves of each construct under a fluorescent stereo microscope. Subsequently, all leaves were incubated in X-gluc staining solution as described above and the number of GUS producing spots was determined for each construct. Values for standardised activities were obtained by dividing the number of GUS-producing spots by the number of GFP-producing cells (FIG. 6). All values were normalised to values obtained with pBI221. The results, summarised in FIG. 6, show that the activities obtained for pMy and pCv under transient conditions in maize leaves are within the range of promoters that have previously been used for high level gene expression in monocot plants: pMy lead to a 1.5-fold higher transient activity than p35S and to nearly half the activity of pUbi; while pCv lead to a 3-fold higher activity than p35S and to nearly equal activity than pUbi.

The results of EXAMPLE 3 show that the sequences presented in SEQ ID NO: 1, SEQ ID NO: 2 and SEQ ID NO: 3 each act as active promoters in vivo. The results further demonstrate that the promoters of SEQ ID NO: 1 and SEQ ID NO: 2 express strongly under transient conditions and that they could provide a valuable tool for gene expression in plants and genetic engineering.

EXAMPLE 4

Assaying Promoter Activity in Plant Cells Under Stable Conditions

Several in vivo test systems were available for assaying the promoter-reporter gene constructs of EXAMPLE 2 under conditions of stable expression in plant cells. These systems were:

1) biolistic gene transfer on sugarcane and tobacco calli using GFP assays after 30 days or more;
2) GUS and GFP assays of transformed and regenerated plants (bananas, sugarcane),
3) Semi-quantitative comparative Western blot analyses of GFP production in transgenic sugarcane; and
4) Quantitative comparative GUS activity assays of different organs of transgenic banana plants.

Using the test system (1) above, the method for sugarcane transformation described in EXAMPLE 3 was used in the manner, which will now be described.

After bombardment, sugarcane calli were placed on selective callus-inducing medium (MSC3) containing 40 $\mu$g/l geneticin (Sigma). GFP activity was monitored at 2 months after bombardment using the methods described in EXAMPLE 3. Green fluorescence appears as grey or white in black and white copies of the photographs.

Figure 7:
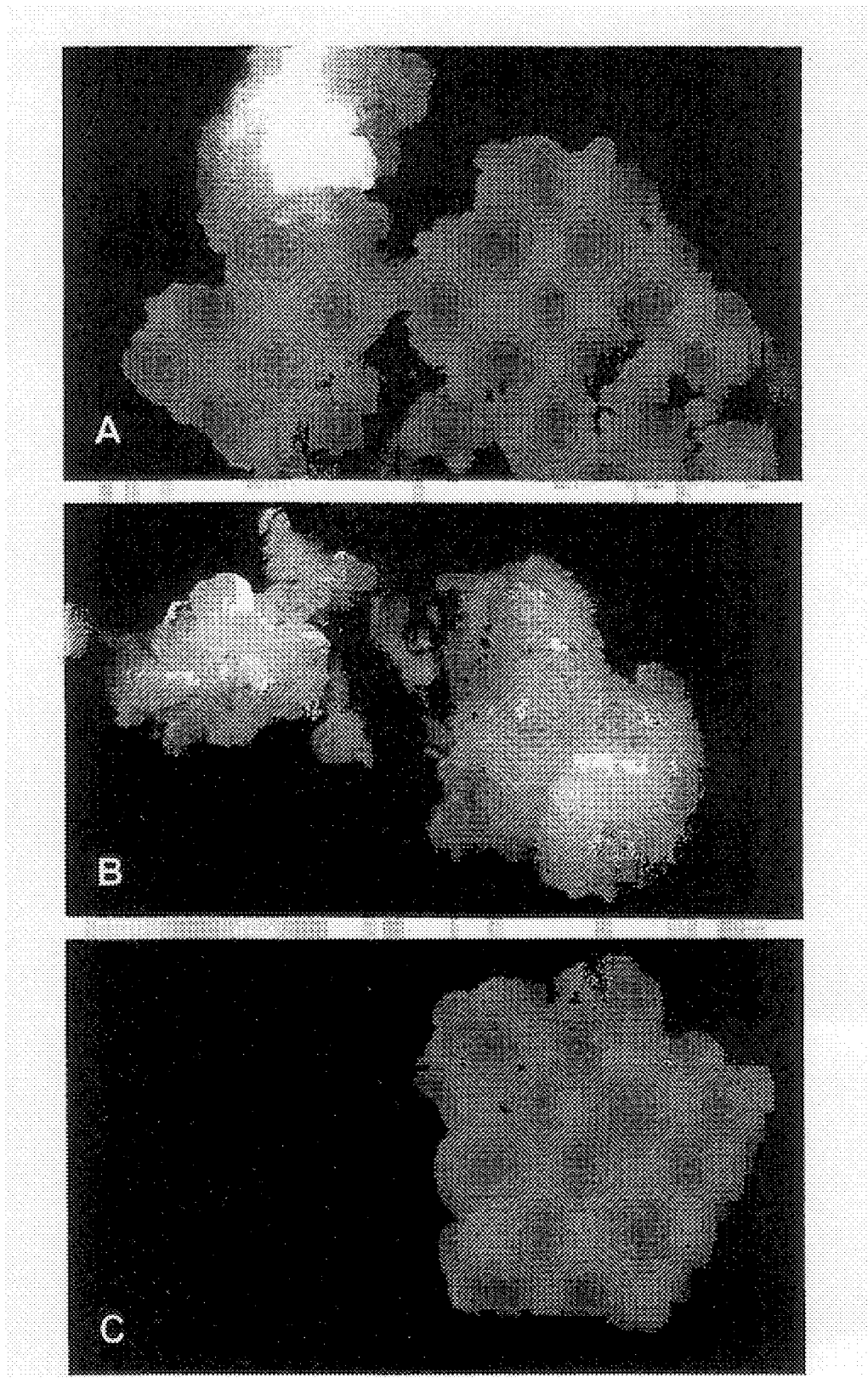
FIGS. 7 to 13 depict the results of stable promoter activity assays using promoter-reporter gene constructs of FIG. 1.

FIG. 7 depicts photographs taken of sugarcane calli bombarded with pMyGFP (FIG. 7A), pCvGFP (FIG. 7B) and pUbiGFP (FIG. 7C) at 2 months after bombardment under fluorescent microscopy. The intensity of fluorescing calli of both constructs pMyGFP and pCvGFP were comparable to those generated by pUbiGFP, indicating that both novel promoters show similar stable activities in sugarcane calli than the maize ubiquitin promoter.

Figure 8:
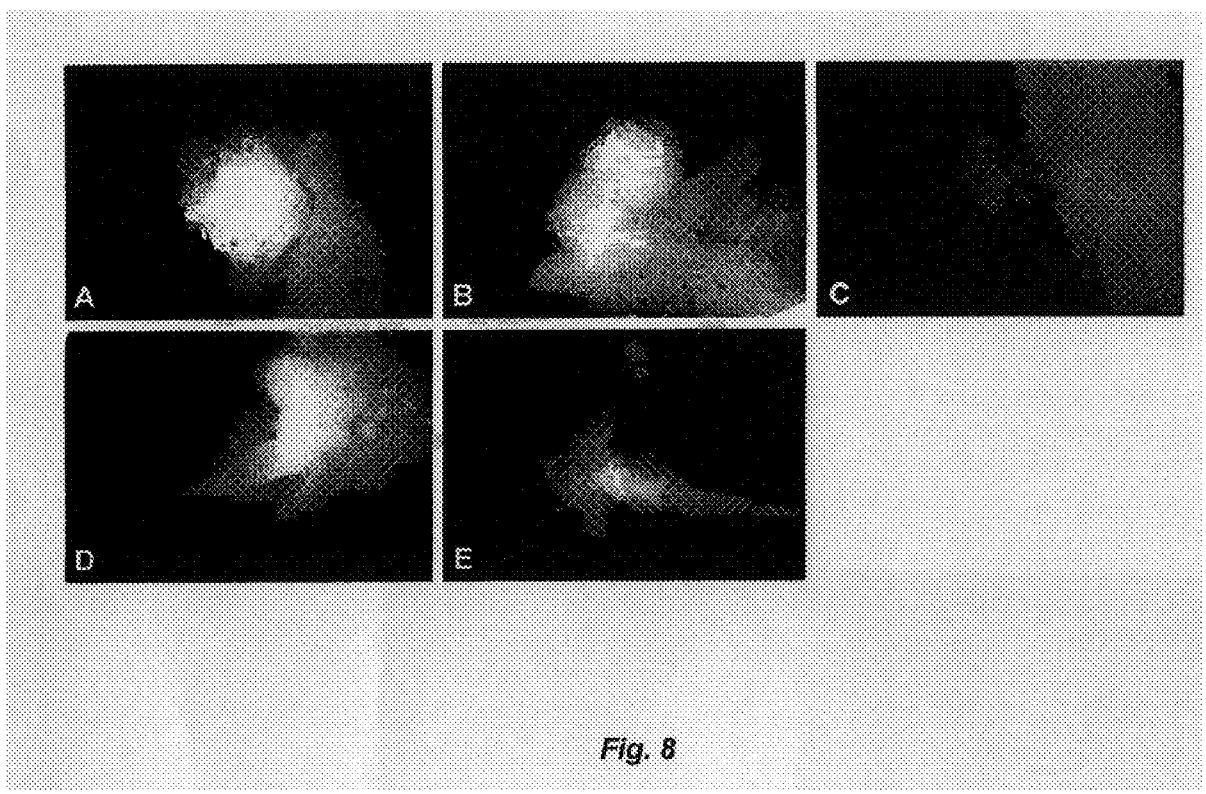

Using test system (1) above, transgenic tobacco calli and plantlets were produced according to the method described by Ellis et al. (*EMBO J.* 6: 11–16 [1987]) using *Agrobacterium tumefaciens* strain LBA4404 containing the binary vectors pBIN-mgfp5-ER, pArtMyGUS or pCvmGFP5-ER. Fluorescent microscopy was used for the analysis of transgenic shoot forming calli and roots transformed with pBIN-mgfp5-ER and pCvmGFP5-ER. FIG. 8 depicts results for tobacco calli and roots transformed with pCvmGFP5-ER (FIG. 8A and FIG. 8C, respectively) and pBIN-mgfp5-ER (FIG. 8B and FIG. 8D) and of untransformed callus (FIG. 8E). While no quantification of promoter activities in tobacco plants was obtained, the results indicate that pCv has a potential to be useful for the transformation of dicot plants.

Using test system (2) above, transgenic sugarcane and banana plants were produced that contained the promoters pMy, pCv and pUbi in fusion with reporter genes.

Forty independent sugarcane calli transformed with pMyGFP from six bombardments, as described above, were used for the regeneration of 125 sugarcane plants that were classified in 21 independent lines. Seventy two independent sugarcane calli transformed with pCvGFP from five bombardments were used for the regeneration of 109 sugarcane plants that were classified in 18 independent lines. For comparison, 40 independent sugarcane calli transformed with pUbiGFP from twelve bombardments were used for the regeneration of 37 sugarcane plants that originated from 16 independent lines. GFP fluorescence was used to identify transgenic cells and to establish their independent status. Plants were transferred to pots in glasshouse facilities and allowed to grow until plant heights reached 70–120 cm (12 months after transformation). To confirm the presence of pMy and pCv fused to the GFP reporter gene, several plants transformed with pMyGFP and pCvGFP were chosen for DNA extraction and PCR analyses using primers that cover both, part of the promoter region and part of the GFP reporter gene. Total plant DNA was isolated from sugarcane leaves (200 mg each) according to the method of Chang et al., *Plant Mol. Biol. Rep.* 9: 389–410 (1993). The presence of the pMy promoter fused to the GFP reporter gene was confirmed by PCR of leaf extracts from plants transformed with pMyGFP using primers MyA (SEQ ID NO: 7, 5'-AGAGGCGCCCCTGGTATTGG-3') and GFP-B (SEQ ID NO: 8.5'-AGATGGTGCGCTCCTGGACG-3') were used to amplify a fragment of approximately 650 bp. The presence of the pCv promoter fused to the GFP reporter gene was confirmed by PCR of leaf extracts from plants transformed with pCvGFP with primers CvA (SEQ ID NO: 9; 5'-CCT AAC GAT GCG GGA AGC CG-3') and GFP-B which were used to amplify a fragment of approximately 550 bp. Extracts from untransformed plants served as negative controls. All primers were synthesised by Pacific Oligos, Lismore, Australia. PCR products of all plants analysed showed the expected band size in DNA gel electrophoresis, while the negative controls showed no bands (data not shown).

Figure 9:
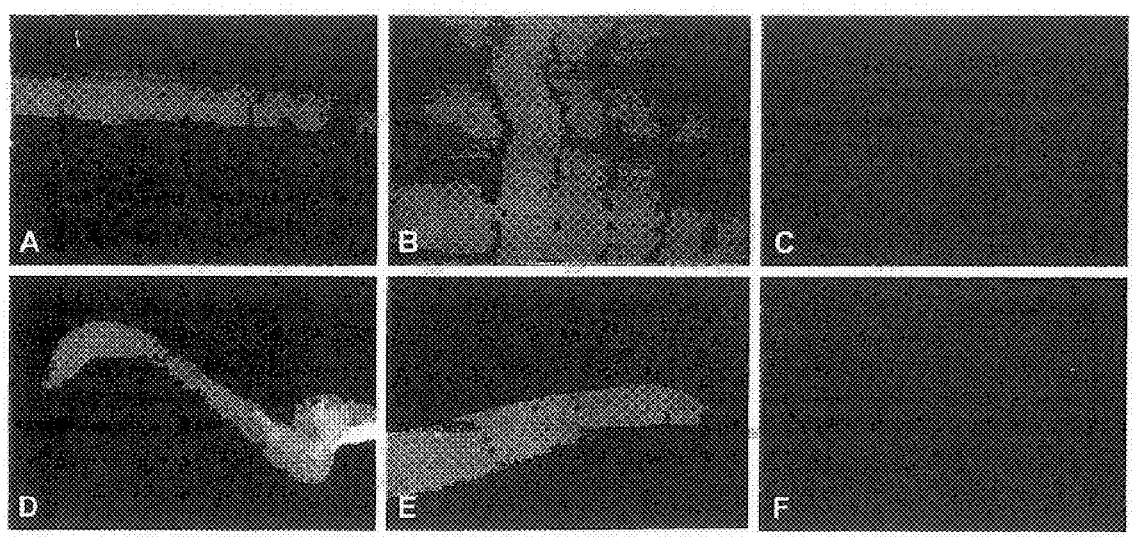

To evaluate GFP production, the youngest leaf from several sugarcane plants of each transgenic was analysed under a stereo fluorescent microscope as described above. The amount of GFP in leaves was evaluated by assigning relative numbers ranging from 0 to 5 (0 being no detectable GFP present and 5 being the highest level of GFP production). In addition, root material was analysed from selected plants (data not shown). Relative numbers for plants transformed with pMyGFP ranged from 0–2, while plants transformed with pCvGFP or pUbiGFP showed a much stronger GFP presence in the leaves with numbers ranging from 0–5. FIG. 9 depicts reproductions of photographs taken under the fluorescent microscope of leaves and roots of sugarcane plants transformed with pMyGFP (FIG. 9A and FIG. 9D, respectively), pCvGFP (FIG. 9B and FIG. 9E, respectively), pUbiGFP (FIG. 9C, leaves only) and of leaves of untransformed control plants (FIG. 9F). Plants transformed with pMyGFP usually showed the strongest expression around vascular leaf tissue, while leaves of sugarcane plants transformed with pCvGFP or pUbiGFP typically showed a constitutive expression throughout all cells analysed. Wound-inducibility of promoters was tested by wounding leaves from sugarcane plants transformed with pMyGFP, pCvGFP and pUbiGFP and from untransformed plants with metal bristles (54 per $cm^2$). An assessment of GFP fluorescence made after 48 h showed increased GFP production around damaged areas of leaves transformed with pCvGFP and pUbiGFP, while no increase in fluorescence could be observed for leaves transformed with pMyGFP or untransfromed leaves. FIG. 9I depicts a portion of a leaf at 48 h after wounding from a sugarcane plant transformed with pCvGFP.

Figure 10:
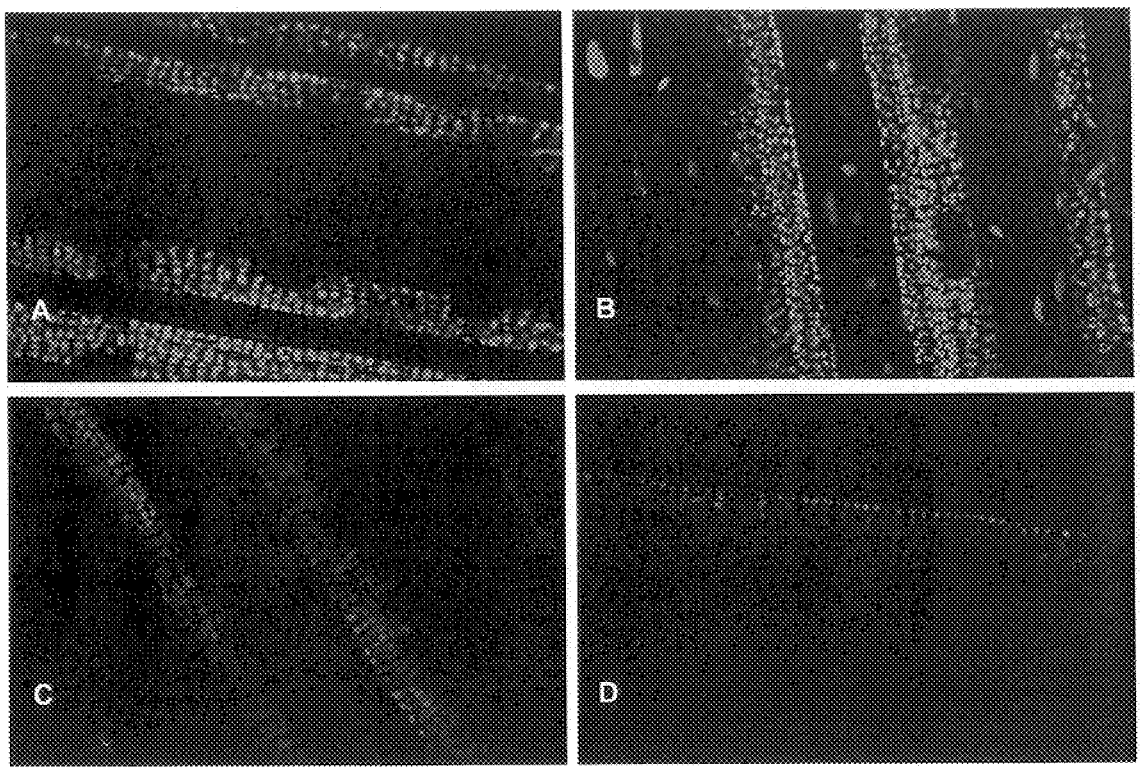
Figure 11:
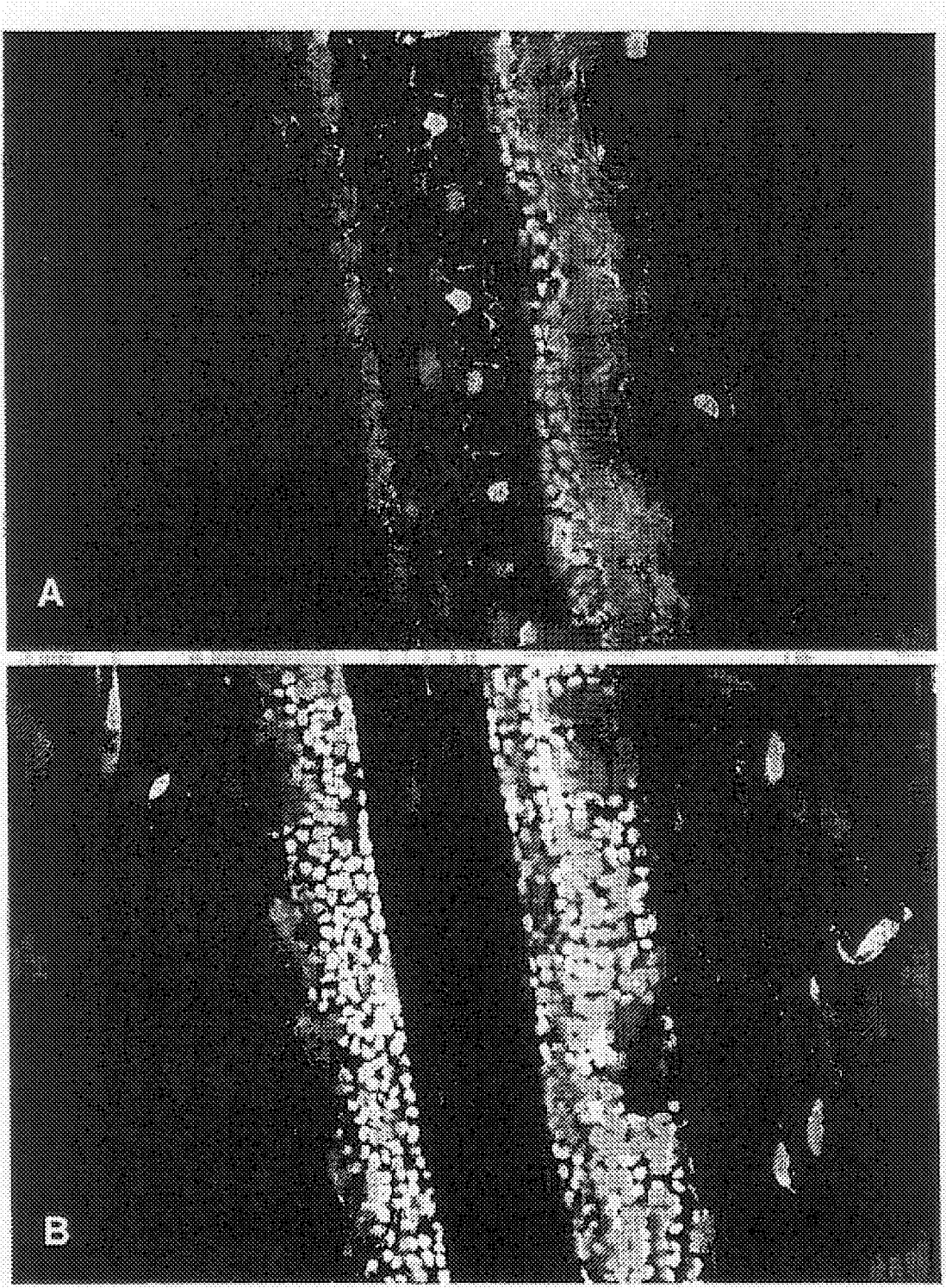

More detailed studies of different leaf cell layers were performed using a confocal microscope (Zeiss) with a Biorad MRC600 light source and appropriate filters for excitation at 488 nm with emission measured at 509 nm. FIG. 10 depicts digital images of superimposed Z series of 9 serial scans at 9 $\mu$m distance of sugarcane leaves facing adaxial-side up from plants that were transformed with pMyGFP (FIG. 10A), pCvGFP (FIG. 10B), pUbiGFP (FIG. 10C) and from untransformed plants (FIG. 10D). It was observed that all cell types of the symplast showed presence of GFP indicating a near-constitutive expression for the promoters tested. As observed previously, the strongest GFP fluorescence could be observed in sugarcane leaves transformed with pCvGFP, followed by pUbiGFP and pMyGFP, while the latter construct lead to lower expression in cells other than those surrounding the vascular tissue (FIG. 10). FIG. 11 depicts two sets of three superimposed images of the Z series shown in FIG. 10B for a leaf transformed with pCvGFP. FIG. 11A covers most of the upper cell layers including the epidermis, while FIG. 11B shows a section through a vascular bundle with its surrounding cells. The accumulation of GFP in the nuclei is noticeable for some cells.

Transgenic banana plants (cv Three Hand Planty) were produced in tissue culture according to the method described by Sági et al., (1995, supra). After co-bombardment of a pAct-neo chimaeric gene construct with pMyGUS and pCv-GUS into banana embryogenic cell cultures, 65 and 61 geneticin-resistant plants have been regenerated, respectively. Plants were subsequently multiplied in vitro using micropropagation.

To confirm the presence of pMy and pCv fused to the GUS reporter gene, several banana plants transformed with pMyGUS and pCvGUS that showed GUS expression were chosen for DNA extraction and PCR analyses using primers that cover both, part of the promoter region and part of the reporter gene. Total plant DNA was isolated from banana leaves according to a modified method of Dellaporta et al., (*Plant Mol. Biol Rep.* 1: 19–21 [1983]). Briefly, 30–100 mg of leaf or root tissue was ground with 500 $\mu$l of extraction buffer (100 mM Tris-HCl, pH 8.0; 50 mM EDTA, pH 8.0;

500 mM NaCl, 10 mM μ-mercaptoethanol; 2% polyvinylpyrrolidone, MW=10,000) in a 1.5 ml microfuge tube. After adding 33 μl of a 20% SDS solution, the mixture was vortexed and incubated for 10 min at 65° C. Subsequently 160 μl of 5 M potassium acetate solution (pH 5.2) was added, the tubes vortexed, and centrifuged in a microfuge for 10 min at 13,000 rpm. After transferring the debris-free supernatant to a fresh tube, the DNA was precipitated by adding an equal volume of isopropanol, vortexing and centrifugation for 10 min at 13,000 rpm. The pellet was carefully washed in 70% (v/v) ethanol and air-dried for 20–25 min with the opening of the tube facing a laminar airflow before resuspension in 20 μl of sterile deionised water.

The presence of the pMy promoter fused to the GUS reporter gene was confirmed by PCR of leaf extracts from plants transformed with pMyGUS using primers MyA (SEQ ID NO: 7) and primer GUS1R (SEQ ID NO: 10; 5'-CTT GTA ACG CGC TTT CCC ACC-3') to amplify a fragment of approximately 450 bp. The presence of the pCv promoter fused to the GFP reporter gene was confirmed by PCR of leaf extracts from plants transformed with pCvGUS using primers CvA (SEQ ID NO: 9) and GUS1R to amplify fragment of approximately 350 bp. All primers were synthesised commercially by Eurogentec (Seraing, Belgium). Extracts from untransformed plants served as negative controls. PCR products of all plants analysed showed the expected band size in DNA gel electrophoresis, while the negative controls showed no bands (data not shown).

Figure 12:
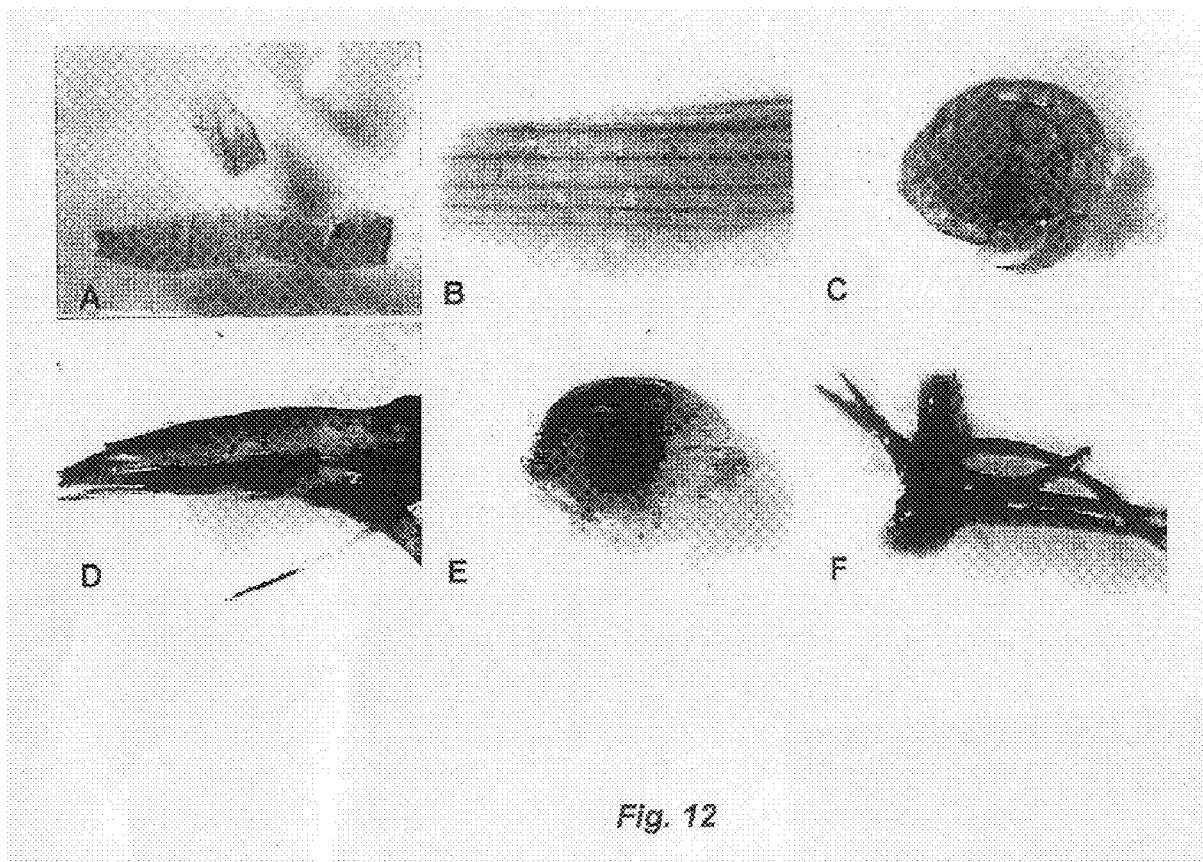
Figure 13:
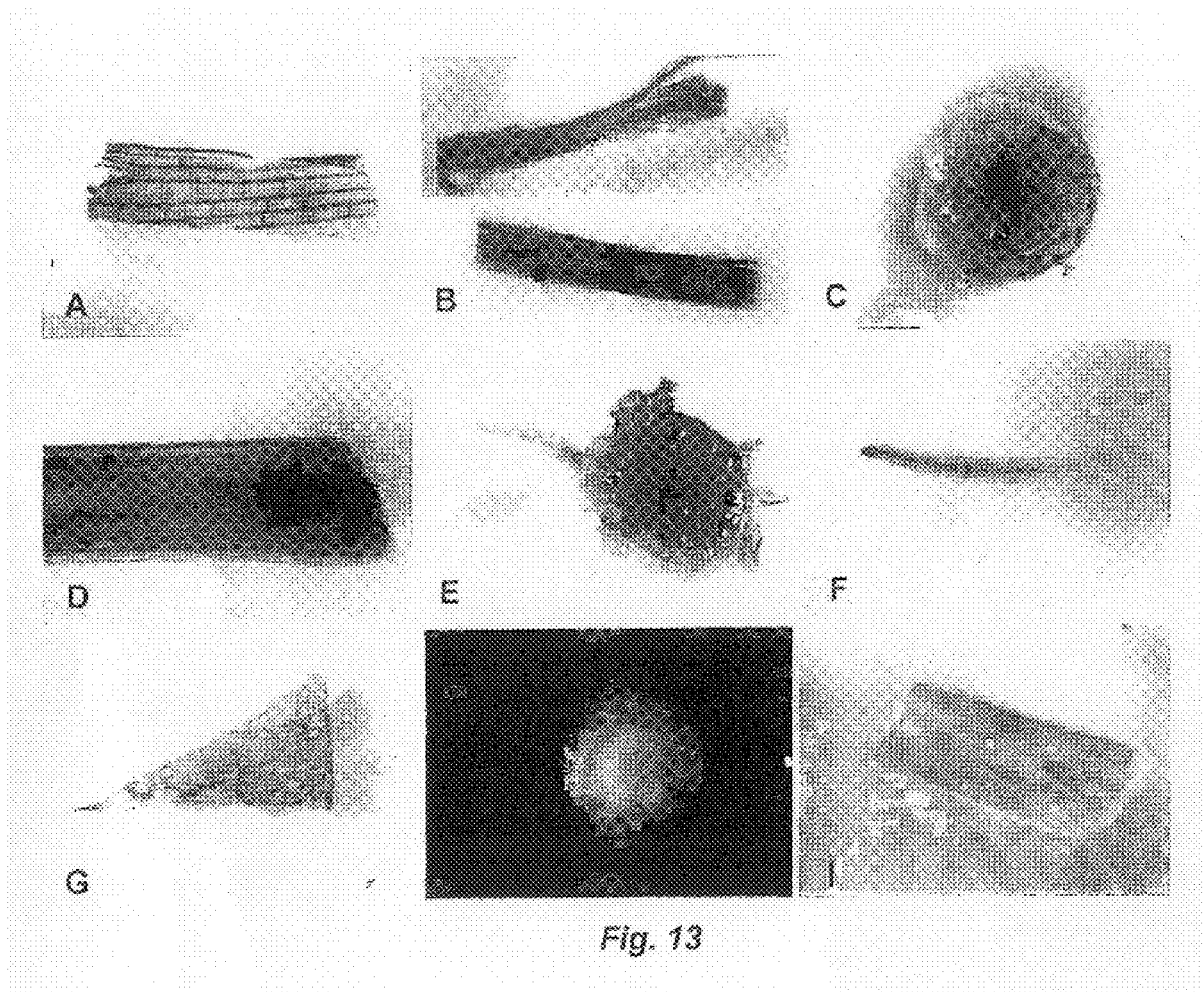

Twenty five transgenic lines transformed with pMyGUS and 30 plant lines transformed with pCvGUS were randomly selected and subjected to a screening by histochemical GUS-staining. GUS staining appears as dark areas in the black and white copies of the photographs. Based on these results, 15 and 12 respective lines were selected for more detailed GUS assays to determine organ- and tissue-specific expression. A summary of the results follows. Generally, two groups of banana plants were found for both constructs: "weak expressors" and "high expressors" with similar tissue specificity. In strong expressors the reaction became visible in 20–30 minutes of X-Gluc staining (100 mM Tris-HCl, pH 8.0; 10 mM EDTA, pH 8.0; 0.5 mM K-ferricyanide; 0.5 mM K-ferrocyanide; 1% ascorbic acid; 0.1% X-Gluc [5-bromo-4-chloro-3-indolyl-β-D glucuronide]: 0.2% SDS) while in weak expressors the first appearance of colouring was delayed (2–3 hours) and the staining intensity rarely reached that of the high expressors. Of the 15 lines transformed with pMyGUS approximately 60% could be regarded as high expressors, while 30% of the 12 lines transformed with pCvGUS showed strong GUS-staining. FIG. 12 and FIG. 13 depict longitudinal and cross sections of different X-glue-stained tissue types of banana plants transformed with pMyGUS or pCvGUS, respectively as well as of untransformed control plants (FIG. 13G, FIG. 13H and FIG. 13I). Both constructs led to similar tissue specificity. Staining intensity was strongest in both, the shoot (FIG. 12D and FIG. 13D) and root apical meristem (FIG. 12F and FIG. 13E) and predominantly in the vascular tissue of root (FIG. 12F and FIG. 13F), in the rhizome (FIG. 12E, FIG. 12F and FIG. 13E) and in the leaf petiole and pseudostem (FIG. 12B, FIG. 12C, FIG. 13B and FIG. 13C). Staining intensities in the upper part of the leaf were usually weaker (FIG. 12A and FIG. 13A) and revealed in some cases a patchy staining pattern that did not seem to be caused by differential substrate uptake during staining. While a constitutive-type expression in banana plants could be observed for both promoters, some lines also showed a more irregular staining pattern that could possibly be due to gene silencing. Control plants that were previously transformed by Sági et al., (1995, supra) with pAHC27 (a plasmid containing pUbi, the GUS reporter gene and the nos terminator; Christensen and Quail, supra) showed a similar near-constitutive staining pattern (data not shown). Leaves, pseudostem, and shoot meristem of an untransformed banana plant that was incubated in X-Gluc staining solution for 24 h showed no GUS activity (FIG. 13G, FIG. 13H and FIG. 13I, respectively). This light brown colour appears as grey in the black and white copies of the photographs.

Figure 14:
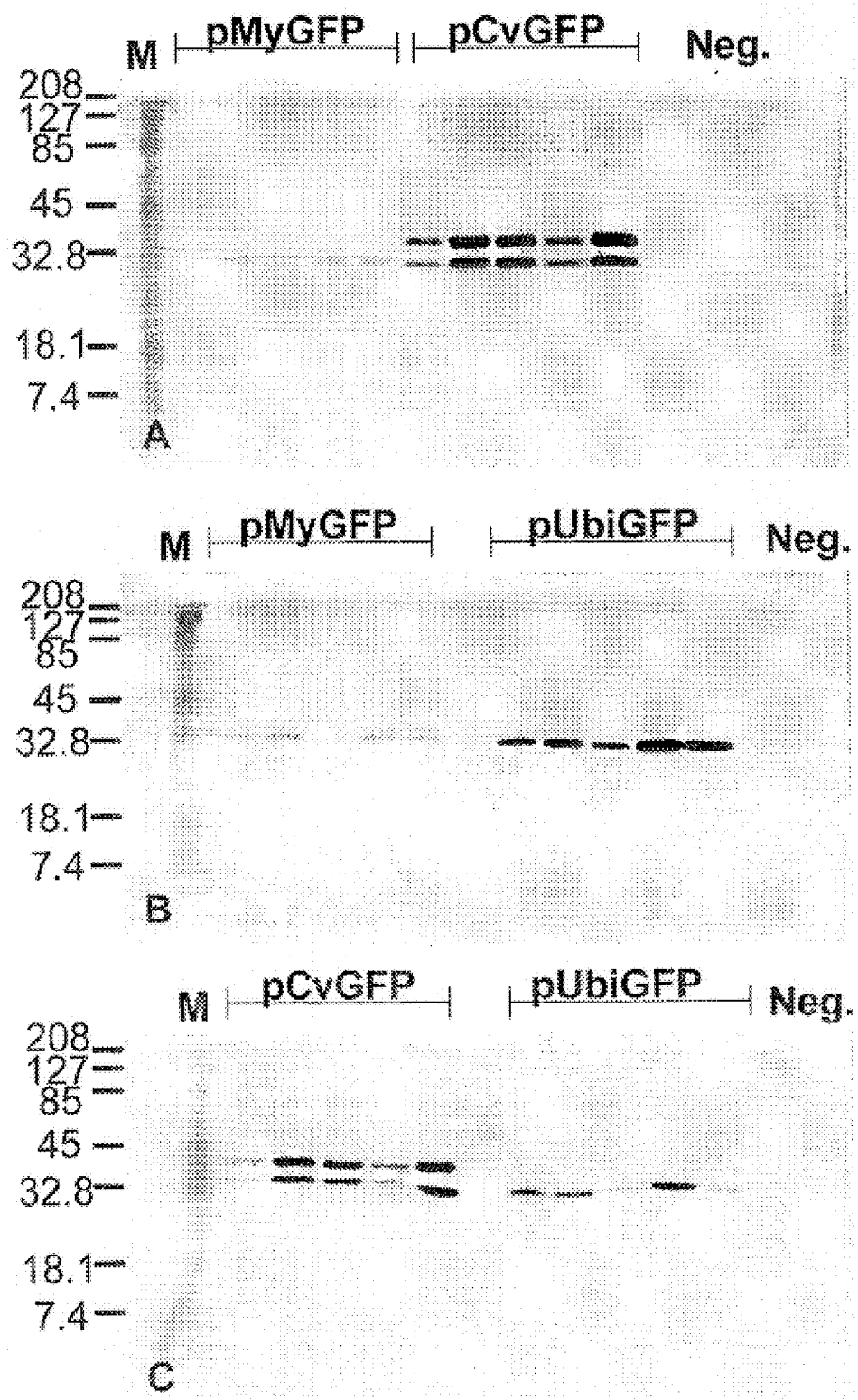
FIG. 14 shows a semi-quantitative promoter activity comparison based on GFP production in transgenic sugarcane leaves.

Using test system (3) above, semi-quantitative Western blot analyses were performed on leaf extracts of the above described transgenic sugarcane plants. This method allows a reliable promoter evaluation that is based on the quantification of GFP produced in the leaves of transgenic plants. According to the previous evaluation with fluorescent microscopy described above, five independent plant lines that showed the strongest GFP production in leaves were selected for each of the constructs pMyGFP, pCvGFP and pUbiGFP. Protein extracts of the youngest leaf from each of these 15 lines were obtained by grinding 150 mg in 1.5 mL of ice-cold extraction buffer containing 50 mM Hepes-KOH, 10 mM $MgCl_2$ 1 mM EDTA, 1 mM EGTA, 5 mM DTT, 1 mM PMSF, 1 mM benzamide, 1 mM benzamidine, 5 mM E-aminocaproic acid, 2 μM leupeptin, 2 μM antipain, 0.1% (v/v) Triton X-100, 2% (w/v) polyvinylpolypyrrolidone, pH 7.5 and approximately 0.1 g of acid washed sand. Western blot analyses were performed according to a method described by Grof et al. in *Sugarcane: Research Towards Efficient and Sustainable Production* (J. R. Wilson, D. M. Hogarth, J. A. Campbell and A. L. Garside, ed's.) pp. 124–126; CSIRO Division of Tropical Crops and Pastures, Brisbane (1996). A commercial antibody preparation consisting of a mixture of two mouse monoclonal antibodies directed against GFP was obtained from Bochringer Mannheim (Cat. No. 1814 460). FIG. 13 depicts comparative immunoblots using the leaf extracts of each of five independent lines of plants transformed with pMyGFP and pCvGFP (FIG. 14A), pMyGFP and pUbiGFP (FIG. 14B) and pCvGFP and pUbiGFP (FIG. 14C). The first lane and the last lane of each immunoblot contain the prestained kaleidoscope size marker in kDa (Biorad) and a leaf extract from an untransformed plant, respectively. In some cases a double band could be detected. This may be due to partial cleavage of a precurser or incomplete denaturing. A relative comparison of all bands depicted in FIG. 14 shows that the intensity was highest for sugarcane plants transformed with pCvGFP, followed by plants transformed with pUbiGFP and plants transformed with pMyGFP. These results correspond to the previous observations using fluorescent microscopy as described above and demonstrate that pCv is a promoter that is suitable for strong expression in transgenic sugarcane plants. Although pMy led to weaker expression, it is nevertheless active in sugarcane plants.

Using the test system (4) above, GUS activity in different organs of transgenic banana plants was quantified using fluorometric GUS assays according to a modified procedure of Jefferson (*Plant Mol. Biol. Rep.* 5: 387–405 [1987]). Briefly, 200–300 mg of plant tissue was ground with sterile washed sand in 400 μl GUS extraction buffer (50 mM sodium phosphate buffer, pH 7.0; 10 mM EDTA, pH 8.0; 10 mM β-mercaptoethanol; 0.1% sodium lauryl sarcosine; 0.1% Triton X-100; 2% polyvinylpyrrolidone, MW=10,000) in microfuge tubes which were subsequently transferred to ice and centrifuged at 10,000 rpm for 10 min. The supernatants were carefully transferred to fresh microfuge tubes.

Figure 15:
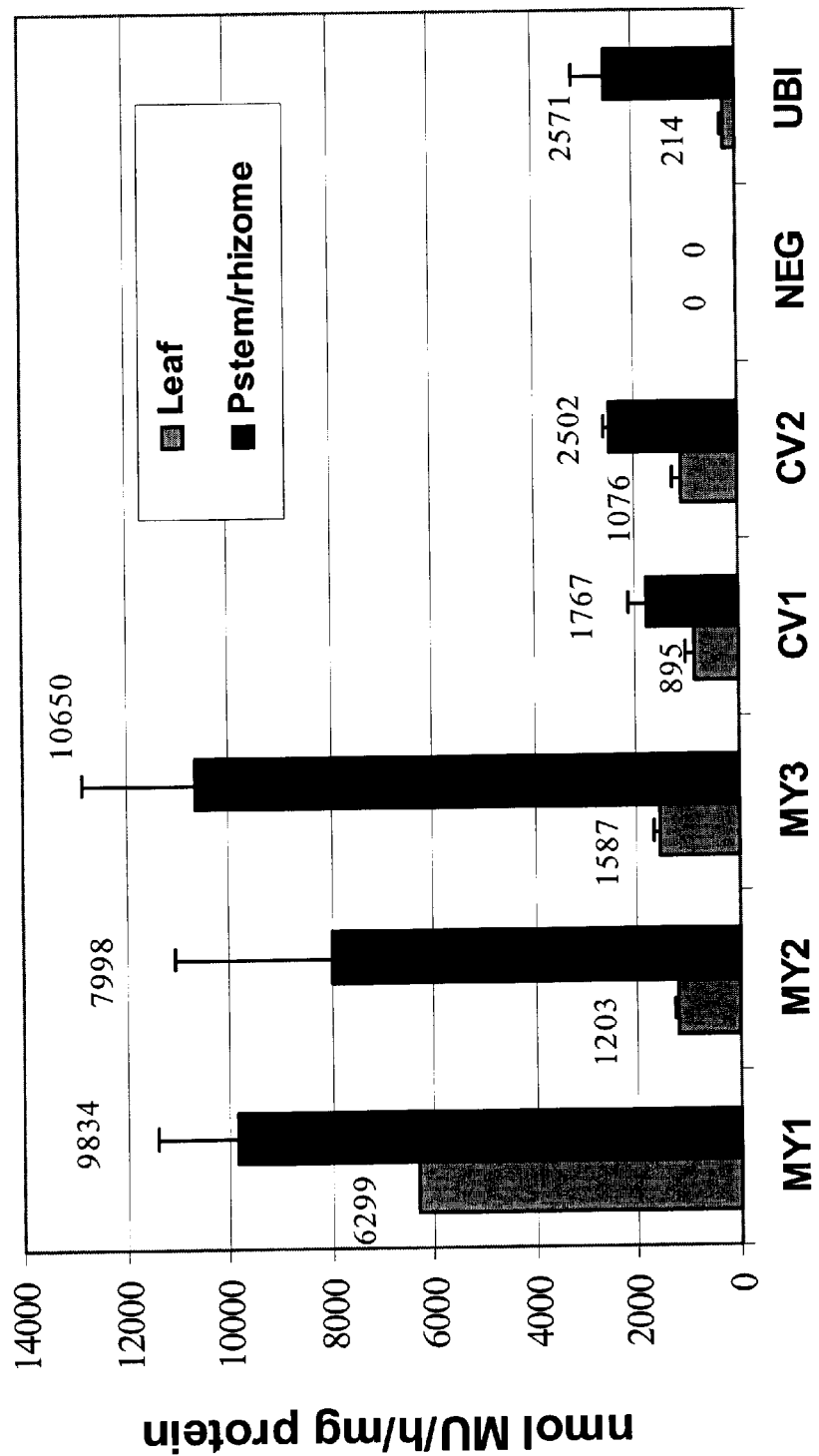
FIG. 15 shows a quantitative promoter activity comparison based on GUS production in different tissues of transgenic banana plants

Protein concentrations were determined by the Bradford assay (BioRad Laboratories). Fluorometric enzymatic GUS assays were carried out for each sample by adding 50 μl of prewarmed (37° C.) protein extracts to 200 μl prewarmed (37° C.) MUG-assay buffer (1 mM 4-methylumbelliferyl β-D-glucuronide (MUG, Sigma) in GUS-extraction buffer containing 20% (v/v) methanol). After incubation at 37° C. for 120 min 10 μl serial dilutions (2–80 fold) were added to 190 μl of 0.2 M Na$_2$CO$_3$ solution in a microtiter plate to stop the reaction. The optical density was measured at 455 nm after excitation at 365 nm on a Luminescence Spectrofluorometer (LS 50B, Perkin Elmer). Protein extracts of untransformed plants were used for the zero sample and 4-methylumbelliferone (MU, Sigma or Duchefa) solutions in GUS extraction buffer with concentrations ranging from 10 μM to 60 μM were used as standards. FIG. 15 summarises the results (in nmol MU per h and mg protein, averaged from at least three measurements with standard deviation error bars) obtained for leaf and pseudostem/rhizome extracts of three lines transformed with pMyGUS (MY1, MY2 and MY3), of two lines transformed with pCvGUS (CV1 and CV2) and of two lines transformed with pAHC27 (UBI, average shown). Plants expressing pMyGUS lead to a 5 to 29-fold higher GUS activity in leaves and to a 3 to 4-fold higher activity in pseudostem/rhizome tissue than comparable plants transformed with pAHC27. Plants expressing pCvGUS lead to a 4 to 5-fold higher GUS activity in leaves and to a similar activity in pseudostem/rhizome tissue than the plants transformed with pAHC27. An untransformed banana plant (NEG) showed no activity.

The results of EXAMPLE 4 show that the sequences presented in SEQ ID NO: 1 and SEQ ID NO: 2 are both active as promoters in transgenic plants under stable conditions. The results further demonstrate that both promoters also express strongly at a rate higher than the maize polyubiquitin promoter under stable conditions in transgenic sugarcane and banana. These results confirm that the promoters of SEQ ID NO: 1 and SEQ ID NO: 2 provide valuable tools for gene expression in plants and for genetic engineering.

EXAMPLE 5

Identification of Putative Promoter Elements

Putative promoter elements were identified using the program Signal Scan of the ANGIS program package, TFSEARCH (Heinemeyer et al., *Nucleic Acids Res.* 26, 364–370 [1998]) and by comparison with putative promoter elements that were identified in promoter sequences of other plant virus genomes of the caulimo- or badnavirus subgroup (e.g. Chen et al., *J. Virol.* 70, 8411–8421 [1996]; Verdaguer et al., *Plant Mol. Biol.* 31, 1129–1139 [1996]; Yin and Beachy, *The Plant Journal* 7, 969–980 [1995]).

FIG. 16, FIG. 17 and FIG. 18 depict putative promoter elements in the core promoter region, identified in the DNA sequence of SEQ ID NO: 1, of SEQ ID NO: 2 and of SEQ ID NO: 3, respectively. These elements include the TATA box (TATA; Breathnach and Chambon, *Ann. Rev. Biochem.* 50, 349–383 [1981]; Bucher, *J. Mol. Biol.* 212: 563–578 [1990]) surrounded by G/C rich regions, the initiator (INI; transcriptional start site; O'Shea-Greenfield and Smale, *J. Biol. Chem.* 267, 1391–1402 [1992], Bucher [1990] supra), the viral C/EBP (CCAAT/enhancer binding protein) site (C/EBP; Graves et al., *Cell* 44, 565–576 [1986]; Bakker and Parker, *Nucl. Acids Res.* 19, 1213–1217 [1991], Grange et al., *Nucl. Acids Res.* 19, 131–139 [1991]), the GATA binding factor 1 (GATA-1; Merika and Orkin, *Mol. Cell. Biol.* 13: 3999–4010 [1993]) and the activation transcription factor (ATF; Rooney et al., *Mol. Cell. Biol.* 10, 5138–5149 [1990]).

It will be appreciated by one of skill in the art that many changes can be made to the promoter and promoter-containing constructs exemplified above without departing from the broad ambit and scope of the invention.

What is claimed is:

1. A promoter operative in a plant cell, said promoter comprising:
   isolated DNA from a badnavirus having a sequence comprising a sequence selected from the group consisting of SEQ ID NO: 1, SEQ ID NO:2, and SEQ ID NO:3;
   or a variant which hybridizes under stringent conditions (0.1×SSPE, 0.1% SDS, 65° C., two washes) to a polynucleotide having a sequence selected from the group consisting of SEQ ID NO: 1, SEQ ID NO:2 and SEQ ID NO:3;
   or a truncated promoter-active portion of any of the foregoing, wherein said plant viral homolog or a plant genome-integrated viral variant or promoter-active portion thereof is operative to express in a plant cell.

2. The promoter according to claim 1, wherein said promoter is a truncated promoter-active portion which has a sequence comprising any one selected from the group consisting of: 1538–2105 of SEQ ID NO: 1, 850–1322 of SEQ ID NO:2, and 859–1297 of SEQ ID NO:3.

3. The promoter according to claim 1, wherein said promoter is a truncated promoter-active portion which has a sequence comprising any one selected from the group consisting of: 1806–2105 of SEQ ID NO:1, 1023–1322 of SEQ ID NO:2, and 998–1297 of SEQ ID NO:3.

4. A DNA construct comprising at least one gene having at least one promoter according to claim 1 operatively linked to a coding sequence.

5. The DNA construct according to claim 4, wherein said coding sequence encodes an RNA or a polypeptide.

6. A method of expressing a product in a plant cell, said method comprising introducing a DNA construct according to claim 4 or an RNA transcript of said construct into cells of a plant, wherein said DNA construct or RNA transcript coding sequence encodes said product.

7. A plant cell which comprises the DNA construct of claim 4.

8. The plant cell according to claim 7, wherein said plant is selected from the group consisting of a monocot, a dicot, a gymnosperm and a fern.

9. The plant cell according to claim 8, wherein said plant is a monocot which is a species selected from the group consisting of sugarcane, banana, maize, millet and sorghum.

10. The plant cell according to claim 8, wherein said plant is a dicot which is a species selected from the group consisting of tobacco, canola, Tipu tree, and *Nicotiana benthamiana*.

11. The plant cell according to claim 8, wherein said gymnosperm is the species radiata pine.

12. A plant, plant tissue or reproductive material of a plant, wherein said plant, plant tissue or reproductive material comprises cells according to claim 7.

13. A transgenic plant, plant tissue, or reproductive material of a plant, wherein said plant, plant tissue or reproductive material comprises cells according to claim 7.

14. A DNA construct comprising:
   1) a first gene having at least one promoter according to claim 1 operatively linked to a coding sequence; and
   2) a second gene having a promoter operatively linked to a coding sequence, wherein the expression product of said second gene coding sequence modulates the activity of the expression product of said first gene coding sequence.

15. The DNA construct according to claim 14, wherein said first gene encodes an RNA or a polypeptide.

16. A plant cell comprising the DNA construct according to claim 14.

* * * * *

SEQUENCE LISTING

```
<160> NUMBER OF SEQ ID NOS:  10

<210> SEQ ID NO 1
<211> LENGTH: 2105
<212> TYPE: DNA
<213> ORGANISM: badnavirus

<400> SEQUENCE: 1
cccaggaata aacacgatta tcagtcgaat tggaaatgcc aaagtttatt caaaattcga      60
cttaaaaagt ggtttccatc aagtagccat ggatcctgaa tccatcccat ggacggcttt     120
cctggctaac aatgagctct atgagtggct tgtcatgccc ttcggtctga agaatgctcc     180
agcaatattc caacgaaaga tggacacctg ttttaaaggt actgaagcct tcattgctgt     240
ttatatagat gatattttag tattttctga gaccgaacaa ttgcatagag accacttaag     300
aaaattcctg gaaatcagta aggccaatgg gctcatatta agcccaacca agatgaaaat     360
aggggtcaaa actattgact tcctaggagc ctctatagga aactccaaga tcaagcttca     420
gcctcatatt atcaagaaaa tagctgactt cgacgatcat aggctgaaag aaacaaaagg     480
tttgagggca tggcttggga tattaaacta tgcaagaaac tacatcccaa acttaggaaa     540
aactctaggc cctctttact ctaagatatc accaaatggg gagaaaagaa tgaacgctca     600
```

-continued

```
ggattgggca ctagtcactc aggttaaaag acaagtccag aacctaccag agctggaatt      660
acccccagaa aaatgtaaaa tggtgataga aacggacggc tgcatggaag gttggggcgg      720
cgtctgtaag tggactactg tcggcaaggc acaagaaaaa gtatgcgcct atgccagtgg      780
aaagtttacc cccatcaaaa gcactattga tgcggaggta caggctgtaa ttaacagcct      840
tgataagttc aaaatatact atttggacaa gaaggagtta ttgatcagaa cagactgtga      900
agctatagtc aggttctata aaagcacagc tcagaacaaa ccctcccggg ttagatggct      960
catgctgacc gacttcatct cggtacgggt ctagaaata aaatttgagc atattaatgg     1020
ctgcgagaat atattggcag actccctctc tagactagtc caaacactgt tacaaggatg     1080
gcagcatcaa cacctaaatg gaatcctact ggctctagaa gaattgtatc aaaagcccaa     1140
cccagaagtt gcgaagaaaa tcgggcagat cattatgaaa gttctggaga gccagctgg      1200 aatacagata aatatgatca ctgaaggacc taaacttcgg tgcgcatgtg aaaagatgc      1260 tgagatagct gtctcccaca cttcgagaaa tcctgaccga ccctttaca aatgccaaag      1320 aaatctgtgc cacatttgga tatggaaaaa cttagtggat gactactttc aaaacttaac     1380
ggcgtggaac agaatctctg aagaacacag aagggaaatg gctcgtgaag aaggtcagaa     1440
tctggaagaa gaagactact gggagaatgt attcaatgag gttttcgacc acgaagaaat     1500
cacggagttc taccctgacg gaggagatcc cggttagaaa caaggaagcg tgaagaggac     1560
ccattacagc tgtgatcgca cccacaagct gtgtcagaaa gaaaggtatg gtgcagggcg     1620
gctagcgctc aattatcttg cttttcagtt ttcaattctg taaatggcag acagagtgag     1680
gtgtcaaagg acgatggggc ccaatgagta cccgctttga ctactttaca atctgaaagc     1740 tatgcttta ttttgttaag ctgatcctga gcctcgggga gccggatcta gcatagtaaa     1800
accagaggcg ccctggtat tggcgctgcg gttttaagcc cacggttttc ggactccatg      1860
agttttgaaa tccgacggct ttagtctgag aaggctcagc ctttctctat ataagggttt     1920
gtaacccctc gttgcaagca gagtcggaaa taccagactg cttacttcga gttttgaaat     1980
cccaataaga atcctcagtt ttcttcatcc ttctttcggt tcacttcctg aaattgggca     2040
agccccatag taaggaaaga tccatttggt gtaattccgc ttcactcctg gtatcagagc     2100
catgt                                                                  2105
```

<210> SEQ ID NO 2
<211> LENGTH: 1322
<212> TYPE: DNA
<213> ORGANISM: badnavirus

<400> SEQUENCE: 2

```
ataataatag agacagatgg ttgcatggaa ggttggggag gagtttgtaa atggaaagaa       60
caatcaggac aaccaagatg gtcagagaag atttgtgctt atgcgagtgg aaagtttaat      120
ccgatcaaga gcacaattga tgcagaaatt caagcagtca tcaacagctt ggataaattc      180
aagatatatt atcttgataa aaaggagttg atcatcagga cggatagtca agcgatagtc      240
agtttctaca agaagagtag tgaccacaaa cccctcaaggg taagatggtt agctttcact      300
gactatatca ctggaacagg attggatgtg aagtttgagc atattgacgg caaggataat      360
gtgctagcag acactctgtc aaggctagta aaaatcatat gccacaagga gaaacatcca      420
tcagaaacaa tattgatcaa cgttgcagaa gaaatacttc agaaaggaag tattggagca      480
aaaagaaagt tgggagaaat gataagtgga tatgaagctt ggatgacaag aatccaagaa      540
cacaaaatca agacactaac acttatcgaa aaaccagttt ttaaatgtgg ttgcaggaaa      600
```

-continued

```
cctgctaggc ttcacacgtc caggacatca agaaatccgg aagagaatt ttactcatgt      660 gaaaataaag catgtttcac ttgggtatgg aaggatcaga ttgatgaata cgttcaagaa      720
gtgatgacgt ggaacgacca agtaagccag ttgccagaag aaccagaagg ctacaatgaa      780
ggatgcacga ttgaagacgc attcgatctg ctagacgtca gcaatgacga tcaatgggca      840
aggtcgtaag ccatgacgta gcggaagtga tggaccccat accactggat ggcactaacc      900
agtgtgacaa ggatacgaga tgccaagtga gctggatagc actcacttta tgtaaagagt      960
ggtctgcgta ccaactccac tatagtctgt ctgaggtgcg atgctgtgtc acgcacaaag     1020
actttagatt cctttgcgtg agatgtacgc aaagcagtgt gtccagagtg tgctgtgacg     1080
cgtcccttgc attattggtg ggtgcaccta acgatgcggg aagccgaact ccctctataa     1140
ataggacccc gtgtattcag ttgcaagcac gcaacacaac gcgagcttac ttctgagaag     1200
aaataagaac aatttgtgct tgaaatacac cttgtgtcaa gagtgtgagt agagcgcaag     1260
atccgtgttg ggaaatccgt gccgttctgg aaatccgtgc cgttctggta tcagagcttt     1320
gt                                                                   1322
```

<210> SEQ ID NO 3
<211> LENGTH: 1297
<212> TYPE: DNA
<213> ORGANISM: badnavirus

<400> SEQUENCE: 3

```
ataatcattg agacggacgg atgtatggat ggttggggtg gcatttgcaa atggaagtta       60
aacaaagggg aaccccgatc cgctgaaaag atctgtgctt atgcaagtgg acgtttcaac      120
cccatcaaag gagctattga cgctgaaata caggctgtta tctacagtct agaaaaattt      180
aagatttact atctcgacaa aaaggagctt atttttaagga ctgacagcaa ggcaattgtc      240
aggttctacg agaaatgttc agaacacaaa ccctctcgtg tccgatggat gactctaact      300
gactacatct cgggatgcgg agttaaggta tattttgaac acattgatgg aaaagataat      360
acacttgcag acgaactatc acgacttgtt caagcaattc tcatcaacaa agaagaatct      420
cctacaatac tatctctaat caaagcaaca acggaggtat acaaaaggaa aatcctatt       480 tccaggagta gattagctct atgcatttcc agagcactgg gtaacaaata tcaagtcaat      540
ttcataactt gggaacaacc ccagctgaag tgtgcctgtg gagaaaatgc cgtactcctt      600
acttcacata ccagccgaaa tccaggacgg agattttata gatgcggtac caacacttgc      660
catgtatggt actgggctga tctaatcgaa gattatattg cgcaacttag caatcttcag      720
aatcttgact caggacaagc agatgatgaa ggatgggcct atcaaacaga agatctgatc      780
aacccagaag atctggccaa ctccgacata gacgaccctc cagaagactc aggactattc      840
caccgacatg atgactaagg cggacgtggt ggacccagca ataatgaagg aatccaattc      900
cttacttcac cgggttcatt attaaagagc ctttacagct cataccctta ttaataatgt      960
tagtgcttgt actattgtgc tttgccagca catactggcg tgtaaaggca tctggttgtc     1020
cccagaaggc ctaaagttag tgcgttccaa cgcacatctg tgtgtaaagg tatctggctg     1080 tttcagacg ctacctccct cttttctcct cccgtccata aggaggca gaacctaagt       1140 gtttcaggca tcgagggaaa tacccatctg cctaatccac ttccagtgtt ttccaaagca     1200
gctgaagttt tcagtctgtg agtagaaagc aagatccttg taagaatttt tgagaagttt     1260
atatttgatt tctccccatc tggtatcaga gcgatat                              1297
```

<210> SEQ ID NO 4
<211> LENGTH: 26
<212> TYPE: DNA
<213> ORGANISM: Artificial Sequence
<220> FEATURE:
<223> OTHER INFORMATION: DNA primer

<400> SEQUENCE: 4
cccaggaata aacacgatta tcagtc                                              26

<210> SEQ ID NO 5
<211> LENGTH: 27
<212> TYPE: DNA
<213> ORGANISM: Artificial Sequence
<220> FEATURE:
<223> OTHER INFORMATION: degenerate DNA primer
<221> NAME/KEY: misc_feature
<222> LOCATION: (1)...(27)
<223> OTHER INFORMATION: n = A,T,C or G

<400> SEQUENCE: 5
cacccccggg mymwngctct gatacca                                             27

<210> SEQ ID NO 6
<211> LENGTH: 29
<212> TYPE: DNA
<213> ORGANISM: Artificial Sequence
<220> FEATURE:
<223> OTHER INFORMATION: degenerate DNA primer
<221> NAME/KEY: misc_feature
<222> LOCATION: (1)...(29)
<223> OTHER INFORMATION: n = A,T,C or G

<400> SEQUENCE: 6
aatagcggcc gcathathat hgaracnga                                           29

<210> SEQ ID NO 7
<211> LENGTH: 20
<212> TYPE: DNA
<213> ORGANISM: Artificial Sequence
<220> FEATURE:
<223> OTHER INFORMATION: DNA primer

<400> SEQUENCE: 7
agaggcgccc ctggtattgg                                                     20

<210> SEQ ID NO 8
<211> LENGTH: 20
<212> TYPE: DNA
<213> ORGANISM: Artificial Sequence
<220> FEATURE:
<223> OTHER INFORMATION: DNA primer

<400> SEQUENCE: 8
agatggtgcg ctcctggacg                                                     20

<210> SEQ ID NO 9
<211> LENGTH: 20
<212> TYPE: DNA
<213> ORGANISM: Artificial Sequence
<220> FEATURE:
<223> OTHER INFORMATION: DNA primer

<400> SEQUENCE: 9
cctaacgatg cgggaagccg                                                     20

```
<210> SEQ ID NO 10
<211> LENGTH: 21
<212> TYPE: DNA
<213> ORGANISM: Artificial Sequence
<220> FEATURE:
<223> OTHER INFORMATION: DNA primer

<400> SEQUENCE: 10
cttgtaacgc gctttcccac c                                              21
```